US008619125B2

(12) United States Patent  
Hori

(10) Patent No.: US 8,619,125 B2  
(45) Date of Patent: Dec. 31, 2013

(54) IMAGE MEASURING APPARATUS AND METHOD

(75) Inventor: Fumio Hori, Tokyo (JP)

(73) Assignee: Olympus Corporation (JP)

( * ) Notice: Subject to any disclaimer, the term of this patent is extended or adjusted under 35 U.S.C. 154(b) by 1371 days.

(21) Appl. No.: 11/690,228

(22) Filed: Mar. 23, 2007

(65) Prior Publication Data

US 2008/0015412 A1    Jan. 17, 2008

(30) Foreign Application Priority Data

Mar. 24, 2006  (JP) ................................ P2006-082393  
Mar. 16, 2007  (JP) ................................. 2007-069229

(51) Int. Cl.  
*A61B 1/04* (2006.01)

(52) U.S. Cl.  
USPC .................. 348/45; 348/51; 348/65; 348/373

(58) Field of Classification Search  
USPC .................................... 348/42, 45, 46, 51, 65  
See application file for complete search history.

(56) References Cited

U.S. PATENT DOCUMENTS

| 5,260,871 | A | 11/1993 | Goldberg |
| 6,120,435 | A | 9/2000 | Eino |
| 6,788,274 | B2 * | 9/2004 | Kakeya ............................. 345/7 |
| 7,463,305 | B2 * | 12/2008 | Wada ........................... 348/373 |
| 7,850,590 | B2 | 12/2010 | Mackel et al. |

| 2003/0060681 | A1 | 3/2003 | Yokota |
| 2004/0135883 | A1 * | 7/2004 | Mochida et al. ................. 348/65 |
| 2006/0012674 | A1 * | 1/2006 | Kao ................................ 348/51 |

FOREIGN PATENT DOCUMENTS

| JP | 2002-209839 | 7/2002 |
| JP | 2003-018617 | 1/2003 |
| JP | 2003-075136 | 3/2003 |
| JP | 2003-140056 | 5/2003 |
| JP | 2004-040480 | 2/2004 |
| JP | 2005-006974 | 1/2005 |
| JP | 2005-287900 | 10/2005 |
| JP | 2006-204898 | 8/2006 |

OTHER PUBLICATIONS

Japanese Office Action mailed Jul. 24, 2012 in connection with corresponding Japanese Patent Application No. 2007-069229 and English translation thereof.

* cited by examiner

*Primary Examiner* — Barbara Burgess  
(74) *Attorney, Agent, or Firm* — Ostrolenk Faber LLP

(57) ABSTRACT

An image measuring apparatus includes: an image acquiring section which images an object to generate input image data; an image processing section which performs image processing on the input image data to generate two output image data; a display which displays display image data corresponding to one of the output image data generated by the image processing section for an input of at least one measurement point; an input unit which inputs a measurement operation on the display image data as a reference; and a measurement section which performs measurement based on another output image data for which image processing by the image acquiring section is different from that for the display image data based on the measurement operation on the input unit.

8 Claims, 18 Drawing Sheets

IMAGE MEASURING APPARATUS AND METHOD

BACKGROUND OF THE INVENTION

1. Field of the Invention

The present invention relates to an image measuring apparatus and an image measuring method. For example, the invention relates to an image measuring apparatus that performs an operation input for image measurement on an image display and performs measurement through calculation processing on image data. Specifically, the invention relates to an image measuring apparatus and image measuring method that can be appropriately used for a stereo measuring endoscope, for example.

This application claims priority from Japanese Patent Application No. 2006-82393, filed Mar. 24, 2006 and priority from Japanese Patent Application No. 2007-69229, filed Mar. 16, 2007, the contents of which are incorporated herein by reference.

2. Description of the Related Art

An image measuring apparatus is known that performs measurement on an object by imaging the object using, for example, an endoscope and performing image processing for the captured image.

As such a known image measuring apparatus, for example, JP-A-2003-140056 (refer to FIG. 1) discloses an endoscope including a projection unit that projects a pattern image indicating a measurement point on an object, imaging units that are disposed so as to be spaced apart from each other by a predetermined distance in order to perform stereo measurement, and a calculation unit that calculates position coordinates of each measurement point on the basis of a captured image.

Further, JP-A-2005-287900 (refer to FIGS. 1 and 2) discloses a measuring endoscope apparatus that includes an optical adapter for stereo measurement so as to perform stereo measurement. The measuring endoscope apparatus includes a calibration jig for acquiring the mask shape of the optical adapter for stereo measurement.

Furthermore, JP-A-2003-18617 (refer to FIGS. 1 and 5) discloses an imaging apparatus that images parallax images with different amounts of exposure, combines the images by performing gradation conversion so as to be weighted to a main object, acquires an image having a wide dynamic range, and performs stereo measurement using the acquired image.

Since the techniques disclosed in JP-A-2003-140056 and JP-A-2005-287900 are different from each other in that the pattern image at a measurement point is projected in JP-A-2005-287900 and corresponding points of parallax images are detected by matching processing in JP-A-2005-287900, for example, measurement purposes or measurement accuracies thereof are different. However, the techniques disclosed in JP-A-2003-140056 and JP-A-2005-287900 have a three-dimensional coordinate position which is detected on the basis of triangulation using parallax images in common. In these endoscopes, an image of an object is displayed on a monitor or the like and an operator determines a measurement section or a measurement position while observing the image.

In the technique disclosed in JP-A-2003-18617, it may be possible to obtain the same effect as a case of actually widening the dynamic range of an imaging unit.

In addition to the technique disclosed in JP-A-2003-18617, as another example of the so-called wide dynamic range processing, there is a case of increasing the number of grayscale levels in an arbitrary brightness region in a pseudo manner by image data calculation processing for performing appropriate gradation conversion.

SUMMARY OF THE INVENTION

According to an aspect of the invention, an image measuring apparatus includes: an image acquiring section which images an object to generate input image data; an image processing section which performs image processing on the input image data to generate two output image data; a display which displays display image data corresponding to one of the output image data generated by the image processing section for an input of at least one measurement point; an input unit which inputs a measurement operation on the display image data as a reference; and a measurement section which performs measurement based on another output image data for which image processing by the image acquiring section is different from that for the display image data based on the measurement operation on the input unit.

In the image measuring apparatus described above, preferably, the image processing section includes an image processing cancelling unit that cancels image processing performed on the input image data.

Further, in the image measuring apparatus described above, it is preferable to further include a processing selection section that selects an image processing operation performed in the image processing section according to a predetermined measurement accuracy condition.

Furthermore, in the image measuring apparatus described above, it is preferable to further include an image processing selection operation section that selectively sets an image processing operation performed in the image processing section. In addition, preferably, the measurement accuracy condition is input by the image processing selection operation section.

Furthermore, in the image measuring apparatus described above, preferably, the processing selection section contains an image processing selection table that stores measurement accuracy of image processing selectable in the image processing section.

Furthermore, in the image measuring apparatus described above, preferably, the image acquiring section is a stereo imaging unit that acquires parallax images and the image processing section generates an output image data corresponding to each of the parallax images. In addition, preferably, the image measurement processing section performs stereo measurement processing from the data of two images to be measured based on the output image data corresponding to each of the parallax images.

Furthermore, in the image measuring apparatus described above, preferably, the image acquiring section is an endoscope containing at least an optical adaptor for stereo measurement, and the image measurement processing section includes a calibration setting unit that performs calibration processing for acquiring the mask shape of an optical system of the endoscope.

Furthermore, in the image measuring apparatus described above, preferably, the image processing performed by the image processing section is wide dynamic range processing.

In addition, according to another aspect of the invention, an image measuring method includes: an image acquiring step of imaging an object to generate input image data; an image processing step of performing image processing on the input image data to generate two output image data; a display step of displaying image data corresponding to one of the output image data generated in the image processing step for an input of at least one measurement point; an input step of inputs a measurement operation on the display image data in the display step as a reference; and a measurement step of performing measurement based on another output image data for which image processing by the image acquiring step is different from that for the display image data based on the measurement operation in the input step.

In the image measuring method described above, the image processing step includes an image processing cancelling step of cancelling image processing performed on the input image data.

Further, in the image measuring method described above, it is preferable to further include a processing selection step of selecting an image processing operation performed in the image processing step according to a predetermined measurement accuracy condition.

DESCRIPTION OF THE PREFERRED EMBODIMENTS

Figure 1:
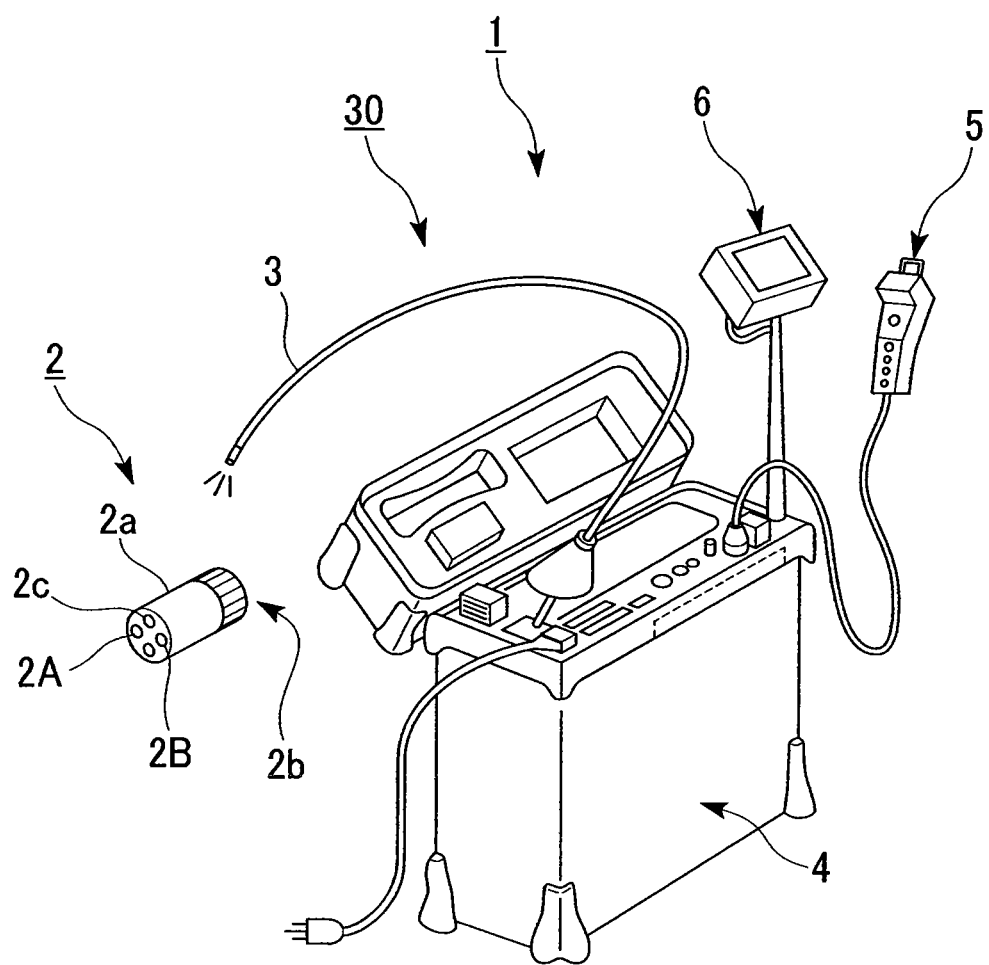
FIG. 1 is a perspective view schematically illustrating the configuration of an image measuring apparatus according to an embodiment of the invention.

Hereinafter, embodiments of the invention will be described with reference to the accompanying drawings. In all of the drawings, the same or corresponding members are denoted by the same reference numerals even if embodiments are different, and common explanation will be omitted.

An image measuring apparatus according to an embodiment of the invention will now be described.

Figure 2:
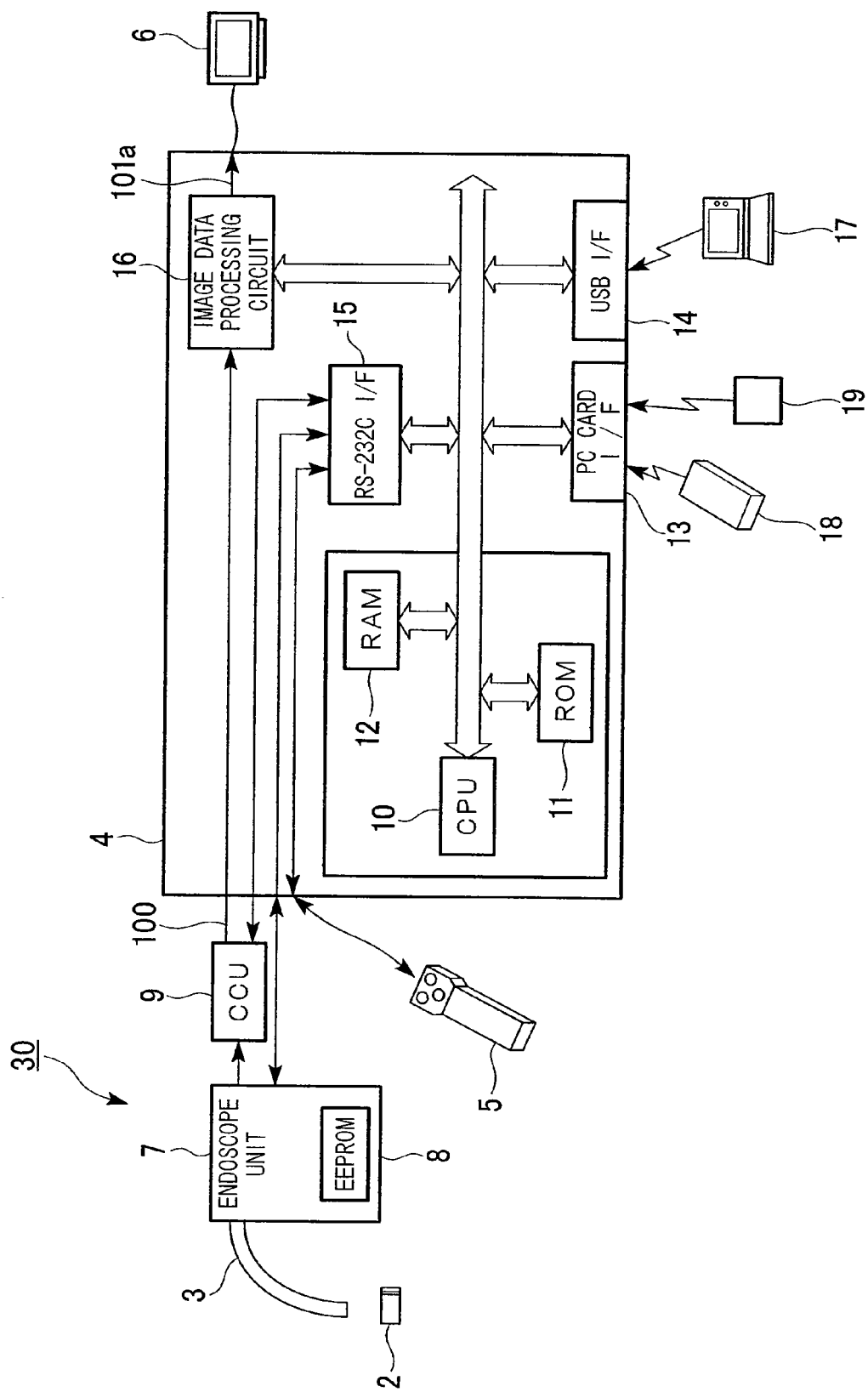
FIG. 2 is a system configuration view schematically illustrating the configuration of a control unit of the image measuring apparatus according to an embodiment of the invention.
Figure 3:
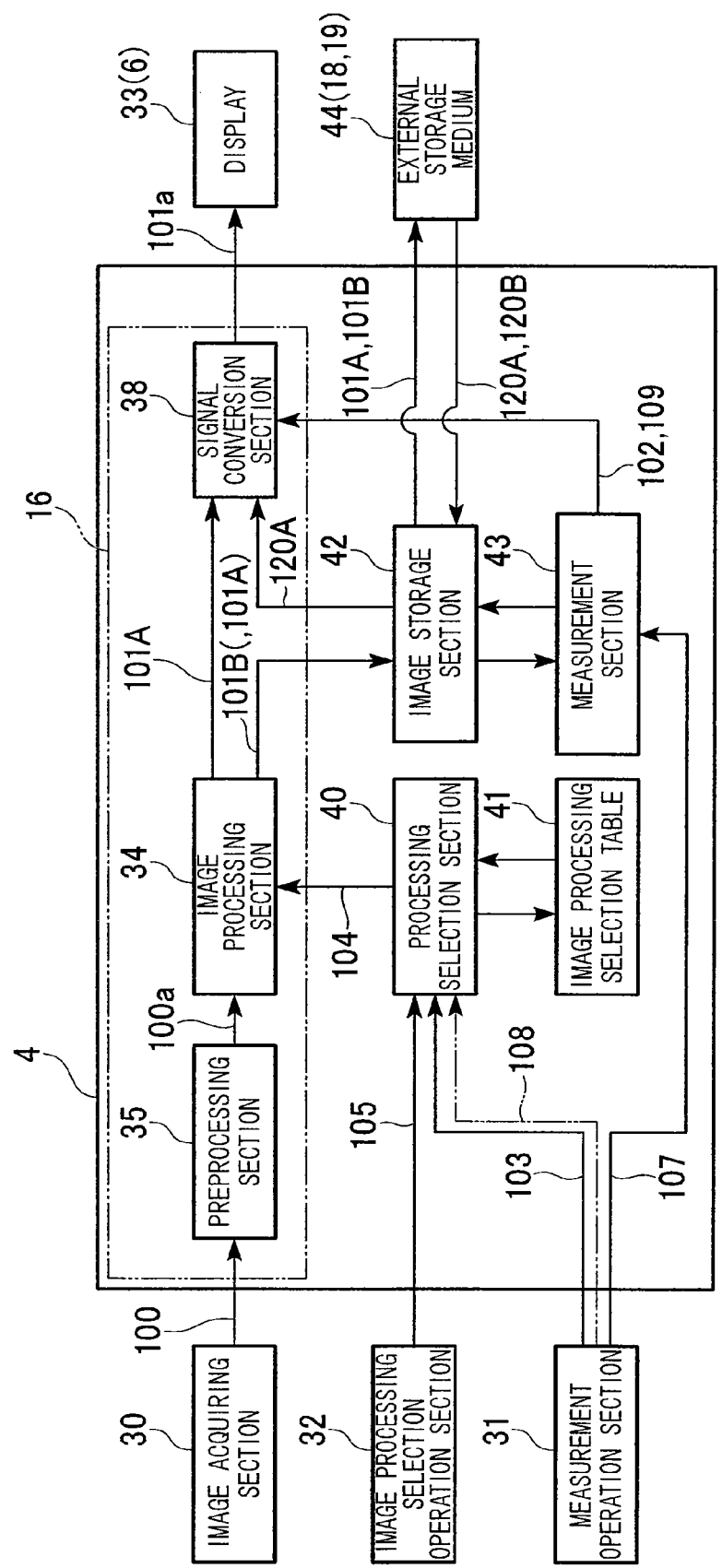
FIG. 3 is a functional block diagram illustrating the configuration of a functional block of a control unit of the image measuring apparatus according to an embodiment of the invention.

FIG. 1 is a perspective view schematically illustrating the configuration of an image measuring apparatus according to an embodiment of the invention. FIG. 2 is a system configuration view schematically illustrating the configuration of a control unit of the image measuring apparatus according to an embodiment of the invention. FIG. 3 is a functional block diagram illustrating the configuration of a functional block of a control unit of the image measuring apparatus according to an embodiment of the invention.

A measuring endoscope apparatus 1 according to the present embodiment is an image measuring apparatus that images an object and performs image measurement on the basis of the image. In addition, the measuring endoscope apparatus 1 according to the present embodiment is an image measuring apparatus that can perform various kinds of observation or image measurement by exchanging an optical adapter provided at a distal end of an endoscope insertion part, properly selecting stored measurement processing programs, or properly adding a measurement processing program. Hereinafter, a case of performing stereo measurement will be described as an example of image measurement.

As shown in FIGS. 1 and 2, the measuring endoscope apparatus 1 is schematically configured to include an optical adapter 2 for stereo measurement, an endoscope insertion part 3, an endoscope unit 7, a camera control unit (hereinafter, simply referred to as 'CCU') 9, an LCD monitor 6 (display), a remote controller 5, and a control unit 4.

In the optical adapter 2 for stereo measurement, object lenses 2A and 2B, which are disposed so as to be spaced apart from each other by a predetermined distance, are disposed within a main adaptor body 2a having an approximately cylindrical shape. In addition, the optical adapter 2 for stereo measurement is detachably mounted on a distal end of the endoscope insertion part 3 using a mounting part 2*b* formed with a female screw or the like.

The positions of the object lenses 2A and 2B differ depending on a direct view type that has a field of view at a front end surface in the axial direction of the optical adapter 2 for stereo measurement or a side view type that has a field of view in the side surface direction of the optical adapter 2 for stereo measurement. In the present embodiment, the direct view type is shown.

Accordingly, the object lenses 2A and 2B are disposed near a light incidence opening provided on the front end surface of the optical adapter 2 for stereo measurement with optical axes thereof toward the axis direction of the optical adapter 2 for stereo measurement.

Moreover, an illumination window 2*c* that causes illumination light guided through the main adaptor body 2*a* to be emitted toward an object is provided on the front end surface of the optical adapter 2 for stereo measurement.

The endoscope insertion part 3 is inserted into the inside of the object so as to image a portion to be measured and then transmits image data to the control unit 4. A mounting part common to a plurality of optical adapters, such as the optical adapter 2 for stereo measurement, is provided in a flexible front end of the endoscope insertion part 3, such that each of the optical adapters is exchangeably mounted.

Although not illustrated, an imaging device, such as a CCD, which captures an image using object lenses of an optical adapter and a light guide that causes the illumination light to be illuminated on an object are provided inside the front end.

The endoscope insertion part 3 has a long and slender tube shape and is flexible over a range from a front end to a base end thereof. Moreover, a signal line of an imaging device, a light guide body, and a wire mechanism used to operate the front end to be bent (all of which are not shown) are disposed inside the endoscope insertion part 3.

In the case when the optical adapter 2 for stereo measurement is mounted in the endoscope insertion part 3, a pair of images with parallax (hereinafter, referred to as 'parallax images') are acquired by the imaging device and two image data corresponding to two object lenses are transmitted to the CCU 9 through the signal line inside the endoscope insertion part 3.

The endoscope unit 7 is configured to include a light source for illumination that generates illumination light guided to the light guide of the endoscope insertion part 3, an electrically-operated bending driving unit for a wire mechanism, and an EEPROM 8 for recording and storing control parameters used to drive the electrically-operated bending driving unit. In addition, the endoscope unit 7 is provided inside the control unit 4 in a state in which the endoscope unit 7 is connected to a base end of the endoscope insertion part 3.

The CCU 9 controls imaging of the imaging device provided in the endoscope insertion part 3 and converts image data acquired from the imaging device into image data, such as an NTSC signal, and then transmits the converted signals to the control unit 4 as input image data 100.

Thus, the optical adapter 2 for stereo measurement, the endoscope insertion part 3, the endoscope unit 7, and the CCU 9 form an endoscope including an optical adapter for stereo measurement and serve as an image acquiring section that forms a stereo imaging unit acquiring parallax images.

The LCD monitor 6 displays an image of an object and other information on the object on the basis of a display image data 101*a* transmitted from the control unit 4. That is, the LCD monitor 6 serves as a display 33 (refer to FIG. 3) that displays an image corresponding to an output image data generated in an image processing section. The image and information are displayed independently or together according to necessity.

In the case of performing stereo measurement as in the present embodiment, the display image data 101*a* corresponding to the input image data 100 of one or both of parallax images are displayed.

Other information displays include, for example, operation input information from an input unit, such as the remote controller 5 to be described later, an operation menu, and a graphic user interface (GUI) for operation (hereinafter, these operation-related displays are collectively referred to as 'operation screen image').

Further, display of a cursor image used at the time of measurement and measurement result information 102 indicating a measurement result or the like are included.

The remote controller 5 is an input unit for performing all kinds of operation input of the measuring endoscope apparatus 1 and is connected to the control unit 4.

For example, an operation related to ON and OFF of a power source and calibration setting, an operation related to an imaging operation, an operation related to illumination, an operation related to driving for bending the endoscope insertion part 3, an operation related to measurement, an operation of selecting the measurement accuracy at the time of measurement, an operation of selecting image processing for an image displayed on the LCD monitor 6, an operation of recording an image from image information, an operation of reading an image recorded in, for example, an external storage medium, or the like can be performed as an operation input performed by the remote controller 5, through a proper user interface. For example, although not shown, a joystick, a lever switch, a freeze switch, a store switch, a measurement execution switch, or the like are provided, such that various kinds of operation input can be performed by executing selective input of an operation menu, executing a direct operation, executing indicating input, or operating GUI displayed on the LCD monitor 6.

That is, the remote controller 5 has a function of an image processing selection operation section 32 (refer to FIG. 3) that selects image processing performed by the control unit 4 and a measurement operation section 31 (refer to FIG. 3) that performs operation input for image measurement on the display screen of LCD monitor 6, so that an operator can change the direction in which an image of an object displayed on the LCD monitor is viewed.

The control unit 4 performs image processing for a captured image and calculation processing for image measurement and also makes an overall control on the measuring endoscope apparatus 1. Accordingly, in the present embodiment, the control unit 4 is configured to include a CPU 10, a ROM 11, a RAM 12, various kinds of input/output interfaces, and an image data processing circuit 16, as shown in FIG. 2.

The CPU 10 loads main programs, which are stored in the ROM 11 or an external storage medium to be described later, to the RAM 12, and executes the program, thereby performing an operation corresponding to each function to be described later.

The input/output interfaces include an RS-232C I/F 15, a PC card I/F 13, a USB I/F 14, and the like.

The RS-232C I/F 15 performs communication for making an operation control between the remote controller 5, the endoscope unit 7, and the CCU 9.

The PC card I/F 13 serves to connect a PC card based on PCMCIA thereto. However, in the present embodiment, the PC card I/F 13 is mainly used to connect a removable external storage medium thereto, load a program for operating the apparatus, or store information on setting or measurement result required for measurement or image information.

For this reason, the PC card I/F 13 is mounted with various kinds of memory cards using flash memory as an external storage medium, for example, a PCMCIA memory card 18 and a compact flash (registered trademark) memory card 19.

The USB I/F 14 is used to connect a USB device thereto. However, in the present embodiment, the USB I/F 14 is provided to detachably connect a personal computer 17 thereto.

In addition, when a personal computer is connected to the USB I/F 14, communication is performed to transmit various kinds of information stored in an external storage medium or various kinds of information stored in an external storage medium connected to the PC card I/F 13 to a storage device or an internal memory of the personal computer 17, to reproduce the information on a display monitor of the personal computer 17, or to execute various kinds of operation input with respect to the control unit 4 instead of the remote controller 5.

For this reason, in the case when the personal computer 17 is connected to the USB I/F 14, the personal computer 17 can also function as the LCD monitor 6 connected to the control unit 4, the remote controller 5, and the external storage medium. Accordingly, for example, a control related to measurement, image processing, image display, or the like can be performed using resources of the personal computer 17 as needed. That is, In this case, the personal computer 17 has functions of the display 33, the image processing selection operation section 32, and the measurement operation section 31 that are shown in FIG. 3. The image processing selection operation section 32 and the measurement operation section 31 are included in the input unit (the remote controller 5).

The image data processing circuit 16 performs image processing, which is designated by the remote controller 5, with respect to the input image data 100 supplied from the CCU 9 to thereby generate output image data 101A and 101B, combines the measurement result information 102 and an operation screen image generated by the CPU 10 as needed, converts the generated signals into, for example, NTSC signals so as to be displayed on the LCD monitor 6, and transmits the converted signals to the LCD monitor 6 as the display image data 101a.

Now, the stereo measurement made by the measuring endoscope apparatus 1 will be described.

The measurement of the measuring endoscope apparatus 1 is made by executing at least first processing for reading optical information from an external storage medium in which optical data of the optical adapter 2 for stereo measurement is recorded, second processing for reading information on the position between an imaging device arranged within a front end of the endoscope insertion part 3 and an object lens system of the optical adapter 2 for stereo measurement, third processing for calculating a positional error of the imaging device of the measuring endoscope apparatus 1 from the positional relationship information and main information on positional relationship between the imaging device of the endoscope and the object lens system of the optical adapter 2 for stereo measurement, which is obtained at the time of production, fourth processing for correcting the optical data from the position error, fifth processing for performing coordinate transformation of an image to be measured on the basis of the corrected optical data, and sixth processing for calculating the three-dimensional coordinates of an arbitrary point by matching two images on the basis of the image for which the coordinate transformation has been performed.

For example, the CPU 10 makes a control such that the first to fourth processing is executed once with respect to the optical adapter 2 for stereo measurement and the result is recorded on the external storage medium as measuring environment data. The first to fourth processing are collectively called calibration processing. Thereafter, when executing the stereo measurement, the CPU 10 makes a control such that the measuring environment data is loaded to the RAM 12 so as to execute the fifth and sixth processing.

In addition, in the case of executing second processing for reading the information on the positional relationship between the imaging device located at a front end and the object lens system of the optical adapter 2 for stereo measurement, the shape of a mask provided in the optical adapter 2 for stereo measurement is acquired and then the shape and position of the mask at the time of production are compared. In this case, acquisition of the mask shape is performed by imaging an object for calibration and then obtaining a white image.

Here, referring to FIG. 3, the configuration of a functional block of the control unit 4 will be described focusing on each functional block relevant to the image data processing circuit 16.

The functional block of the control unit 4 is schematically configured to include a preprocessing section 35, an image processing section 34, a signal conversion section 38, a processing selection section 40, an image storage section 42, and an measurement section 43. Here, the preprocessing section 35, the image processing section 34, and the signal conversion section 38 are included in the image data processing circuits 16.

The preprocessing section 35 executes preprocessing, such as brightness level adjustment or noise removing processing, with respect to the input image data 100 transmitted from an image acquiring section 30 including the optical adapter 2 for stereo measurement, the endoscope insertion part 3, the endoscope unit 7, and the CCU 9 if needed, temporarily stores a processed result in a region of the RAM 12 prepared for calculation processing, and transmits one-frame image information including a pair of parallax images to the image processing section 34 as an input image data 100a.

In the case when the preprocess is not needed, for example, when a satisfactory input image data 100 is acquired by processing of the CCU 9, the preprocessing section 35 may not be provided. In addition, in the case when a function of the preprocessing section 35 is included in image processing of the image processing section 34, the preprocessing section 35 may not be provided.

The image processing section 34 is configured to be able to execute image processing, which is selected from a plurality of image processing including processing in which image processing is not performed as will be described later, through two systems. Further, the image processing section 34 selects image processing in each system on the basis of a control signal 104 transmitted from the processing selection section 40, performs image processing on each input image data 100a which has been subjected to preprocessing in the preprocessing section 35, generates the output image data 101A and transmits the output image data 101A to the signal conversion section 38, and generates the output image data 101B and transmits the output image data 101B to the image storage section 42.

In addition, the output image data 101A and 101B may be different signals but also be the same signals on which the same image processing is performed.

The signal conversion section 38 transmits the output image data 101, which is transmitted from the image processing section 34, to the display 33 as the display image data 101a. In this case, it is possible to combine the output image data 101A with other image data, such as an operation screen image, as needed. Moreover, in the case when the measurement result information 102 generated in the measurement section 43 is transmitted, it is possible to generate the display image data 101a in a state in which the measurement result information 102 is also combined.

The processing selection section 40 selects two-system image processing performed in the image processing section 34 on the basis of a control signal 105 and a measurement start signal 103 that are transmitted from the image processing selection operation section 32 and the measurement operation section 31.

When the control signal 105 is received, the input image data 100a is processed in approximately real time in image processing selected by the control signal 105 to thereby generate the display image data 101a, and the control signal 104 that is transmitted to the display 33, such as the LCD monitor 6, and is used to set an operation mode is generated.

On the other hand, when the measurement start signal 103 is received at a proper timing, image processing for parallax images is selected on the basis of a measurement accuracy condition to be described later.

The image processing selection operation section 32 serves to allow an operator to select image processing for changing the direction in which an image of an object displayed on the LCD monitor is viewed. Accordingly, the image processing selection operation section 32 is displayed as an operation menu, which is displayed on the LCD monitor 6, before the start of measurement and can be selected from the operation menu by the use of the remote controller 5 or the like. In addition, if necessary, even after the measurement has started, the operation menu can be properly called to change the viewing direction.

For example, a white void occurs in a bright portion of an image or black blurring occurs in a dark portion of the image depending on an imaging environment or an illumination condition, and accordingly, it may be difficult to distinguish the measurement position or measurement point of an object. In this case, a gray scale conversion can be performed in a bright region or a dark region.

As an operation menu corresponding to the above situation, options, such as white void correction, black blurring correction, and the like, are displayed, and each correction level can be selected as high, middle, or low, for example. For example, if the black blurring correction and middle level are selected, a selected value is stored in the RAM 12 and the control signal 105 corresponding to the value is generated to be then transmitted to the processing selection section 40.

At this time, measurement accuracy in a case of making a measurement using an image for which each image processing has been performed may be displayed on the operation menu, according to an operator's need, for example, for the sake of convenience.

Processing selection when the measurement start signal 103 is transmitted to the processing selection section 40 is performed on the basis of a measurement accuracy condition that is set in advance before acquiring image data to be measured.

Therefore, the control unit 4 contains an image processing selection table 41 in which the relationship between all image processing performed by the image processing section 34 and each measurement accuracy is described, such that the processing selection section 40 can refer to the image processing selection table 41. For example, when the line width of a line image or the dot size of a dot image, which is to be measured, within a specific brightness range changes, the measurement accuracy varies according to the change. In this case, however, the measurement accuracy can be calculated theoretically or experimentally from a level of change of the line width or dot size.

Types of image processing executable by the image processing section 34 are expressed as a combination of parameters of image processing to be described later, stored in the ROM 11 as two-dimensional or multi-dimensional table data corresponding to types of parameters and the number of levels, and appropriately loaded to the RAM 12 by the CPU 10 and is then used.

In the present embodiment, the measurement accuracy conditions can be set beforehand by the remote controller 5 when initially setting the measurement condition. For example, in the case of distance measurement, a condition such as ±0.1 mm is set as the measurement accuracy condition and is then stored in the RAM 12. Moreover, in the case of setting a set condition for measurement by reading the set condition for measurement from an external storage medium 44, the measurement accuracy conditions may also be stored in the external storage medium 44 such that a read value is automatically stored in the RAM 12 together with other setting conditions.

The processing selection section 40 receives the measurement start signal 103 from the measurement operation section 31 provided in the remote controller 5, acquires the measurement accuracy of current image processing, which is set corresponding to the control signal 105 from the image processing selection operation section 32, from the image processing selection table 4, and compares the acquired measurement accuracy with a predetermined measurement accuracy condition.

Then, if the measurement accuracy is not sufficient, other image processing that satisfies the measurement accuracy is selected from the image processing selection table 41. Furthermore, if the measurement accuracy is sufficient, the current image processing is selected. Then, the control signal 104 is generated corresponding to each measurement accuracy and is then transmitted to the image processing section 34.

In addition, when the measurement accuracy on the image processing choice table 41 becomes the same so that image processing can select uniquely in the processing selection section 40, selection rank is described on the image processing choice table 41, or the selection rule of image processing when measurement accuracy is the same is set as the processing selection section 40.

The image processing section 34 may execute 'n' types of image processing. If it is necessary to distinguish these types of image processing, the image processing is referred to as processing (0), processing (1), . . . , and processing (n−1) (n is an integer larger than or equal to two).

Processing (0) cancels image processing and generates a signal, which does not change the brightness gradation of the input image data 100a transmitted from the preprocessing section 35, as the output image data 101A or 101B.

Other processing (1) to (n−1) is wide dynamic range (hereinafter, simply referred to as 'WDR') processing for changing various kinds of parameters in order to properly convert the brightness gradation of the input image data 100a. That is, when specific image processing is selected by the processing selection section 40, a WDR parameter stored in the ROM 11 is called and then image processing is performed on the basis of the called WDR parameter so as to generate the output image data 101A or 101B.

Examples of processing (2) to (n) will now be described briefly.

Figure 4:
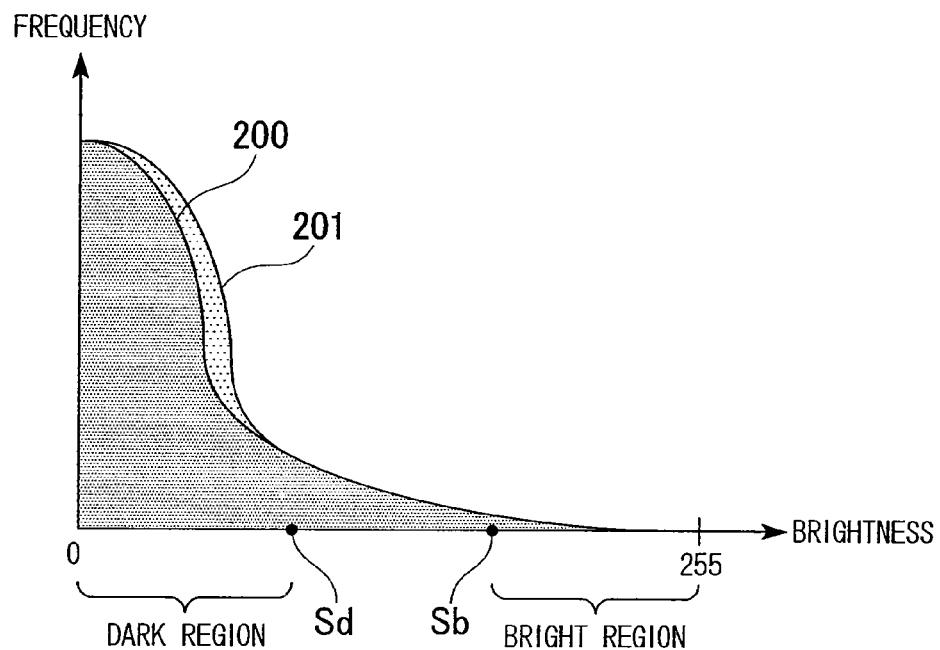
FIG. 4 is a histogram illustrating a first example of the change of brightness distribution before and after WDR processing of the image measuring apparatus according to an embodiment of this invention.
Figure 5:
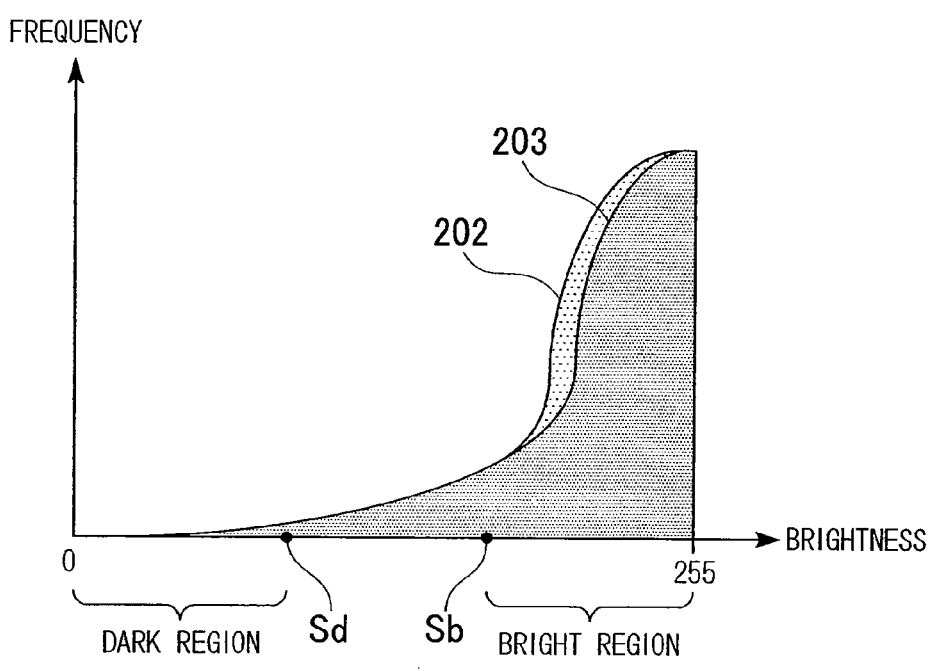
FIG. 5 is a histogram illustrating a second example of the change of brightness distribution before and after the WDR processing of the image measuring apparatus according to an embodiment of this invention.
Figure 6:
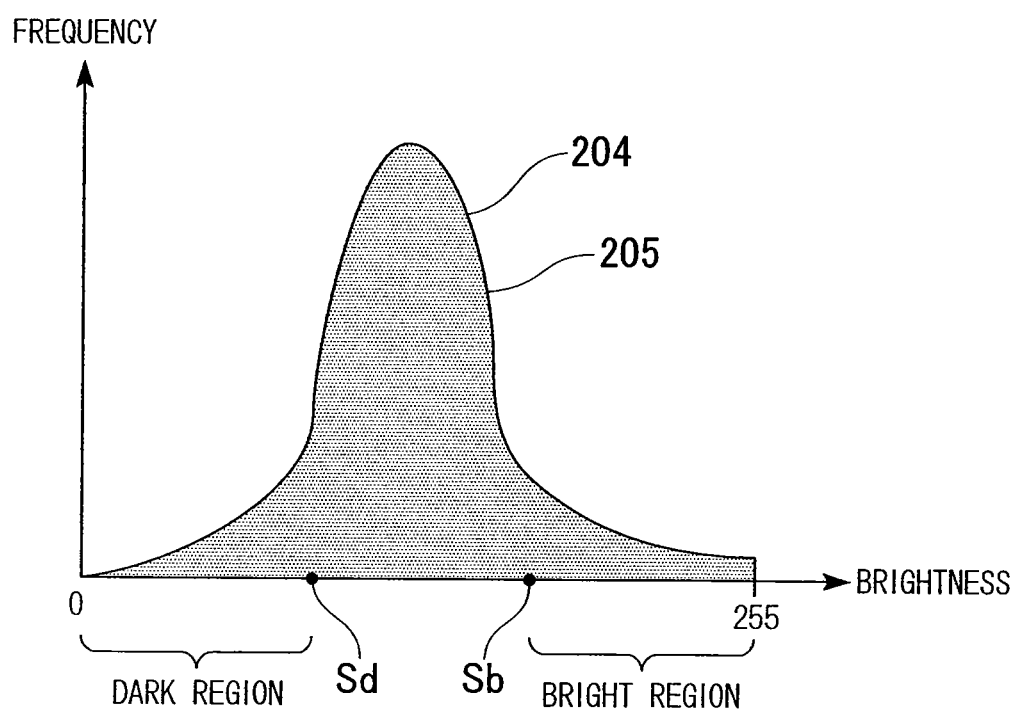
FIG. 6 is a histogram illustrating a third example of the change of brightness distribution before and after the WDR processing of the image measuring apparatus according to an embodiment of this invention.

FIGS. 4, 5, and 6 are histograms illustrating first, second, and third examples of change of brightness distribution before and after WDR processing of the image measuring apparatus according to an embodiment of this invention, respectively. A horizontal axis of each of the drawings indicates the brightness. A vertical axis of each of the drawings indicates a frequency.

In the present embodiment, in the WDR processing, the brightness of image data within a specific brightness region is converted on the basis of a predetermined gradation curve.

In an example of using 256 gray-scale levels, a brightness region to be processed is as follows. That is, a low-brightness processing region that forms a dark portion is set as a region having a brightness of 0 to Sd (where, Sd<255) and a high-brightness processing region that forms a bright portion is set as a region having a brightness of Sb to 255 (where, Sd<Sb<255). That is, (0, Sd) and (Sb, 255) are WDR parameters concerning a brightness region in this case.

Further, conversion of the brightness of each processing region can be made using other proper WDR parameters. As a simplified example, a dark portion is expressed to be shifted to a lower brightness side and a bright portion is expressed to be shifted to a higher brightness side, and intensity indexes of 0 to 100% can be set as WDR parameters. Moreover, intensity indexes, such as 0%, 50%, and 100%, may be selected as a low level, a middle level, and a high level, respectively.

FIG. 4 illustrates an example of performing WDR processing with a dark portion as the middle level and a bright portion as a low level in a case when the brightness distribution of the input image data 100a is inclined toward the dark portion, as shown by brightness distribution 200. Referring to brightness distribution 201 after the processing, relatively high brightness data increases in data within the dark region. That is, black blurring is reduced. In this case, as dark portion data decreases, for example, a black line image and a point image deform so as to be thin. Accordingly, in the case of using the images for measurement, the measurement accuracy is influenced.

FIG. 5 illustrates an example of performing the WDR processing with a bright portion as the middle level and a dark portion as a low level in a case when the brightness distribution of the input image data 100a is inclined toward the bright portion, as shown by brightness distribution 202. Referring to brightness distribution 203 after the processing, relatively low brightness data increases in data within the bright region. That is, white void is reduced. In this case, as bright portion data decreases, for example, a white line image and a point image deform so as to be thin. Accordingly, in the case of using the images for measurement, the measurement accuracy is influenced.

FIG. 6 illustrates an example of performing the WDR processing with both a bright portion and a dark portion as a low level in a case when the brightness distribution of the input image data 100a concentrates at the middle brightness, as shown by brightness distribution 204. In this case, the brightness distribution 205 after the processing approximately overlaps the brightness distribution 204, such that the brightness distribution concentrated at the middle brightness is maintained. That is, since the brightness distribution hardly deforms due to the WDR processing, the measurement accuracy does not change either.

Since the image storage section 42 serves to store the output image data 101A and 101B, which are transmitted from the image processing section 34, as still image data, the image storage section 42 is provided in the RAM 12.

The measurement section 43 performs image measurement using the still image data stored in the image storage section 42 as image data to be measured and generates a measurement GUI image 109 required for a measurement operation input.

In the present embodiment, the stereo measurement is performed on the basis of well-known algorithms. For example, when a measurement point is input on a display image of the LCD monitor 6 by means of the measurement operation section 31, information on the position of a corresponding point of each of the parallax images corresponding to the measurement point is acquired by matching processing based on each brightness information, and image processing for converting the acquire information into three-dimensional position coordinates on the basis of a principle of triangulation.

For example, measurement information 107, which is transmitted to the measurement section 43 and is acquired through a GUI that allows a positioning cursor on the LCD monitor 6 to operate by the use of the remote controller 5 or the like, is used as the information of a measurement point.

A measurement result of the stereo measurement is transmitted to the signal conversion section 38, as the measurement result information 102, together with a measured distance, a mark of a measurement point, and the like, is combined with an image of the output image data 101A in the signal conversion section 38, and is then displayed on the display 33.

Next, an operation of the measuring endoscope apparatus 1 will be described.

Before starting measurement, measurement conditions including a measurement accuracy condition is set. In this case, an operator may input the measurement conditions using the remote controller 5, or it is possible to read conditions stored in the external storage medium. The measurement accuracy condition is stored in the RAM 12.

In addition, the operator selects image processing used for display from an operation menu displayed on the LCD monitor 6. Then, the control signal 105 is transmitted to the image processing section 34, such that desired image processing, for example, the processing (1) is selected from the 'n' image processing.

Thereafter, the endoscope insertion part 3 mounted with the optical adapter 2 for stereo measurement is inserted into an object and then moves toward a desired measurement position of the object by adjusting a front end of the endoscope insertion part 3 to be properly bent using the remote controller 5.

An image, which is formed on an imaging device through the optical adapter 2 for stereo measurement, is transmitted as the input image data 100 to the control unit 4 through the CCU 9. Then, an image for which the processing (1) already set has been performed is displayed on the LCD monitor 6. The operator sets the measurement position of the object while observing the image.

Then, a positioning cursor for setting a measurement point is displayed. For example, in the case of performing distance measurement, two measurement points are designated. Then, an operation input, which is, for example, to press a measurement start switch on the measurement operation section 31 of the remote controller 5, is performed.

The measurement operation section 31 transmits the measurement start signal 103 to the processing selection section 40 and the measurement information 107 to the measurement section 43.

The processing selection section 40 automatically selects image processing that satisfies a predetermined measurement accuracy condition with reference to the image processing selection table 41. For example, in the case when the measurement accuracy condition is not satisfied by the processing (1), another processing (i; where, $2 \leq i \leq n-1$) that satisfies the measurement accuracy condition is selected and the control signal 104 corresponding to the selected processing is transmitted to the image processing section 34.

If the measurement accuracy condition is not satisfied even by the processing (1) to (n), the processing (0) is selected. In this case, since the image processing is cancelled, deterioration of the measurement accuracy due to the image processing does not occur. That is, the processing selection section 40 is included in an image processing cancelling unit.

Further, in the case when the measurement accuracy condition is satisfied by the processing (1), the processing (1) is also selected as image processing for an image to be measured.

The output image data 101A, for which image processing has been performed in the image processing section 34, is displayed on the display 33 through the signal conversion section 38. In addition, the output image data 101B, for which image processing has been performed in the image processing section 34, is stored as still image data in the image storage section 42.

When the output image data 101B is stored in the image storage section 42, the measurement section 43 starts an image measurement operation on the basis of the measurement information 107. Then, a measurement result is transmitted as the measurement result information 102 to the signal conversion section 38.

The image processing section 34 generates the display image data 101a, which is obtained by combining the measurement result information 102 with the output image data 101A by means of the signal conversion section 38, and transmits the display image data 101a to the LCD monitor 6. Thus, an image based on the display image data 101a is displayed on the LCD monitor 6.

Next, a measurement operation of the measuring endoscope apparatus 1 will be described on the basis of an example of a flow chart and a display screen.

Figure 7:
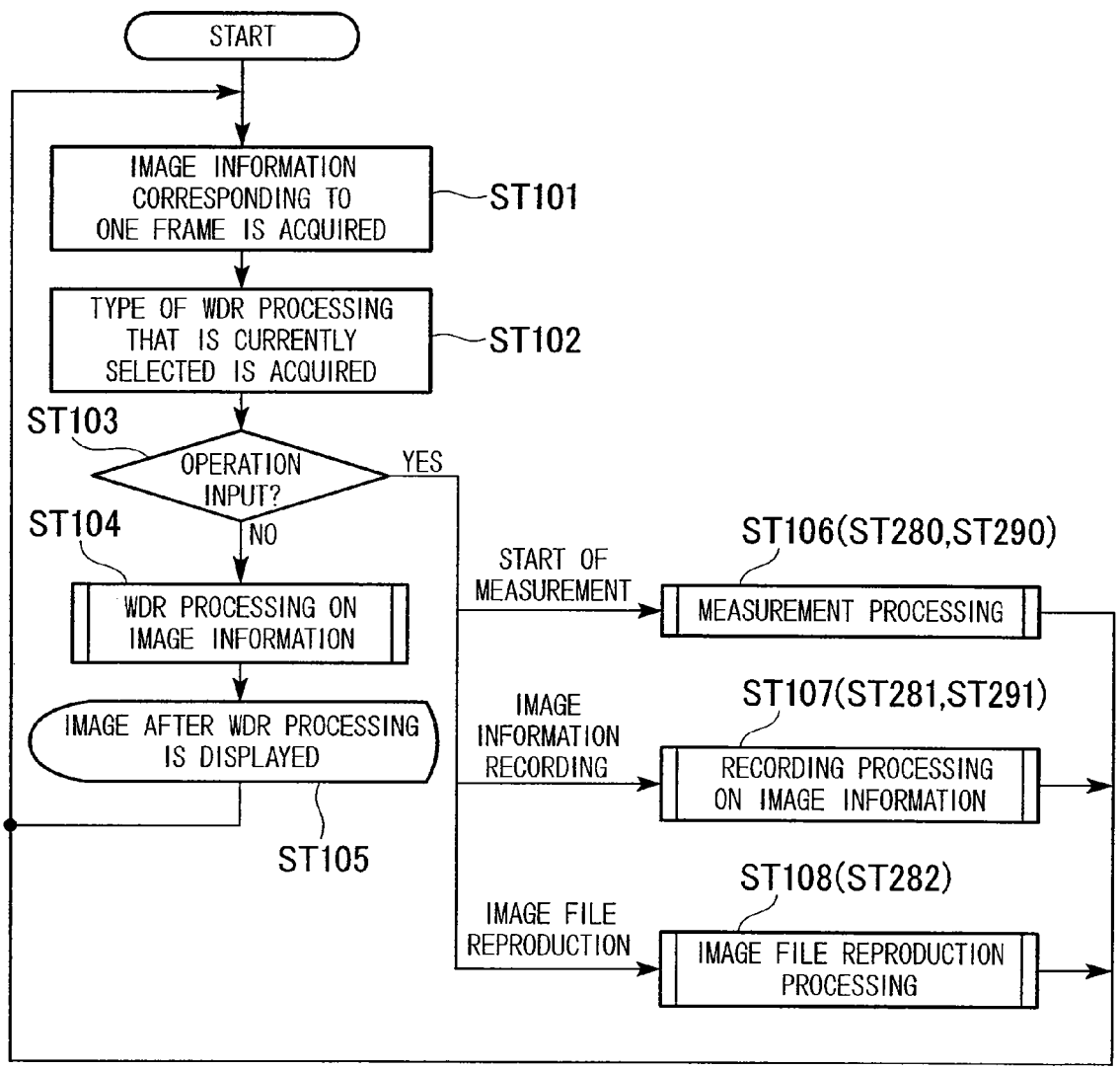
FIG. 7 is a flow chart illustrating an operation of the image measuring apparatus according to an embodiment of the invention.
Figure 8:
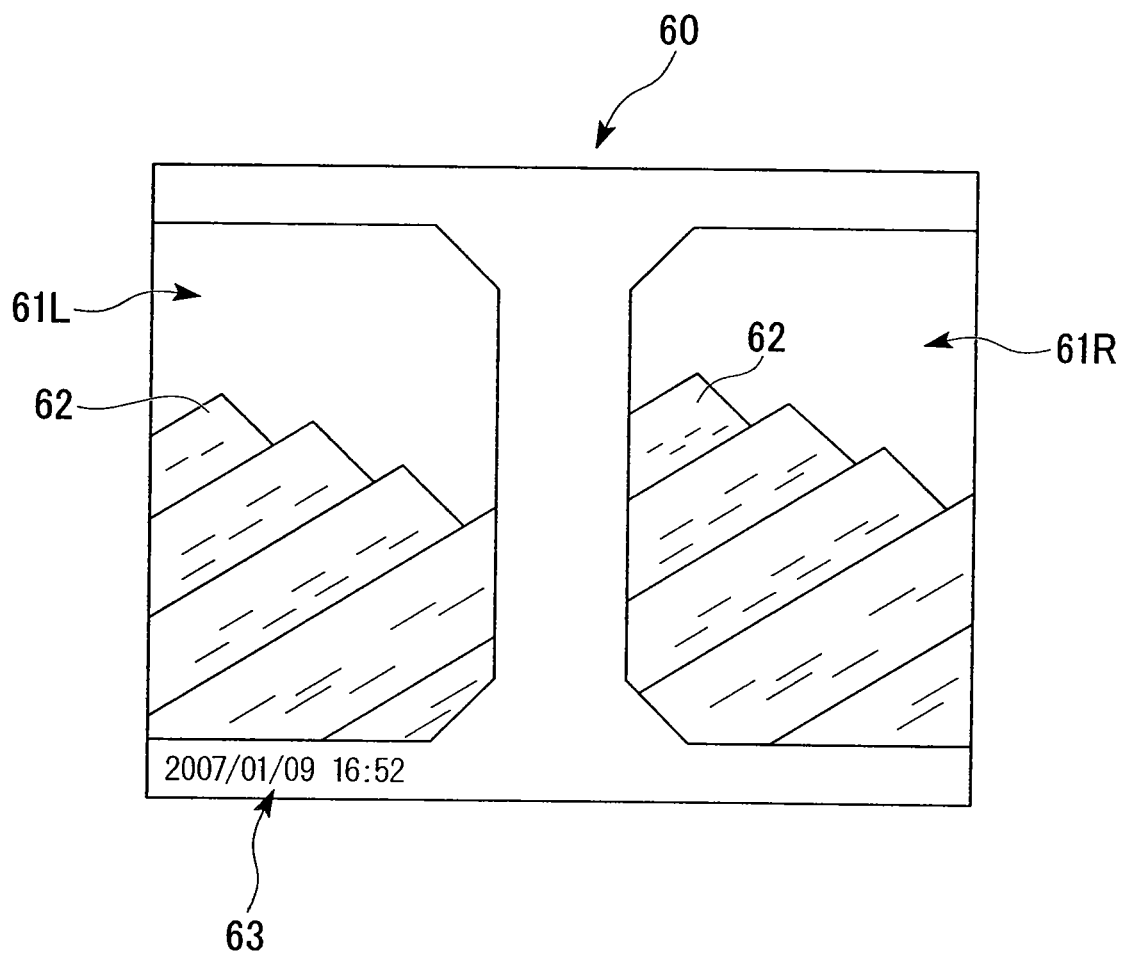
FIG. 8 is an explanatory view schematically illustrating an example of a display screen in an image display mode of the image measuring apparatus according to an embodiment of the invention.
Figure 9:
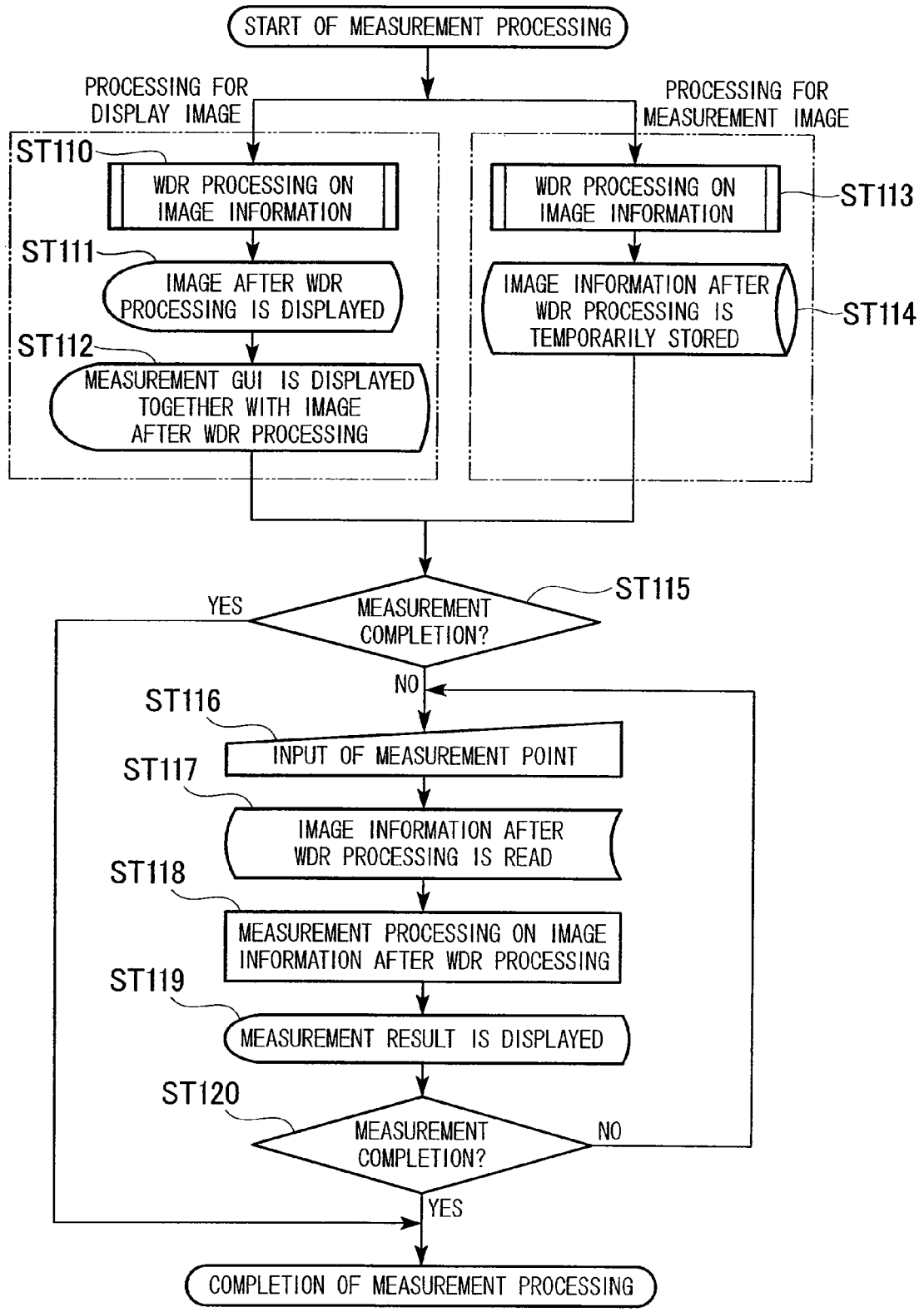
FIG. 9 is an explanatory view schematically illustrating an example of a display screen in an image display mode of the image measuring apparatus according to an embodiment of the invention.
Figure 10A:
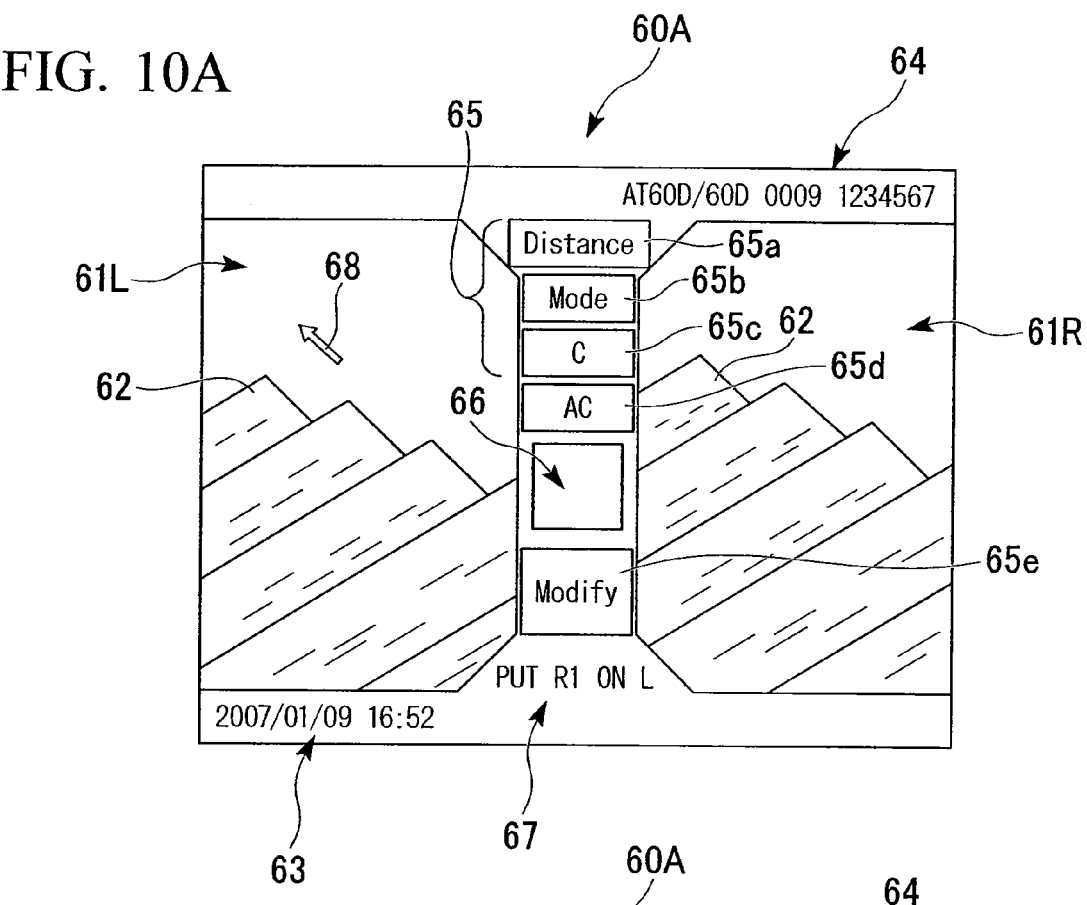
FIG. 10A is an explanatory view schematically illustrating an example of a display screen in a measurement mode of the image measuring apparatus according to an embodiment of the invention.
Figure 10B:
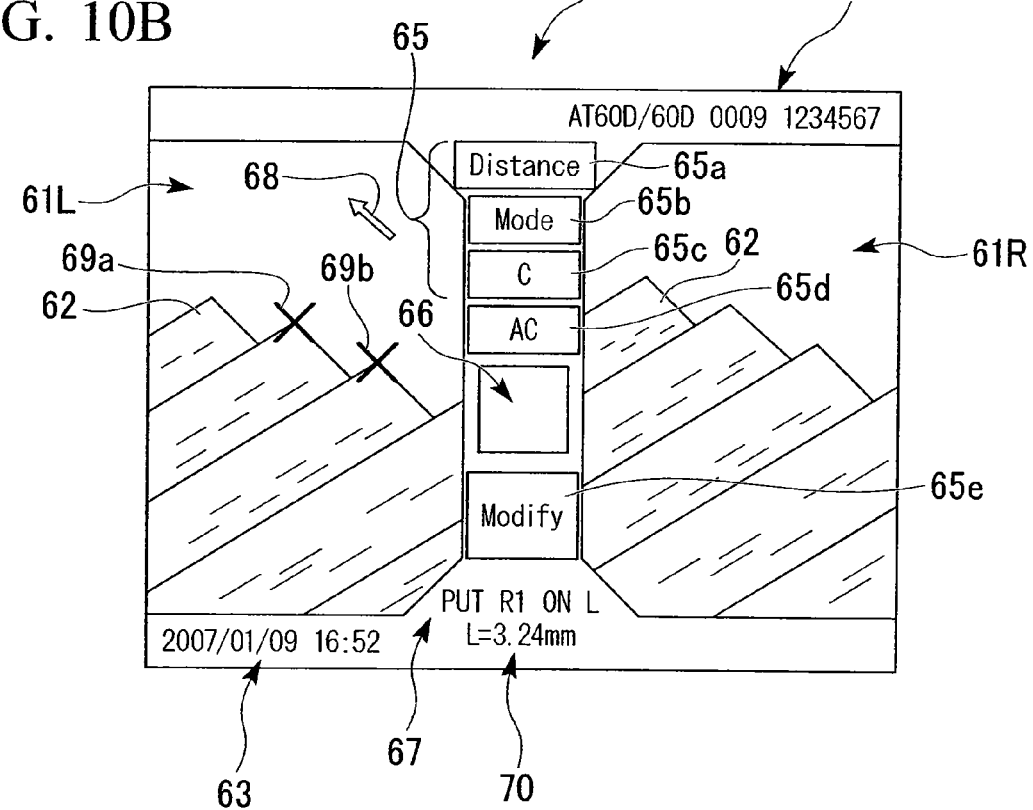
FIG. 10B is an explanatory view schematically illustrating another example of the display screen in the measurement mode of the image measuring apparatus according to an embodiment of the invention.
Figure 11:
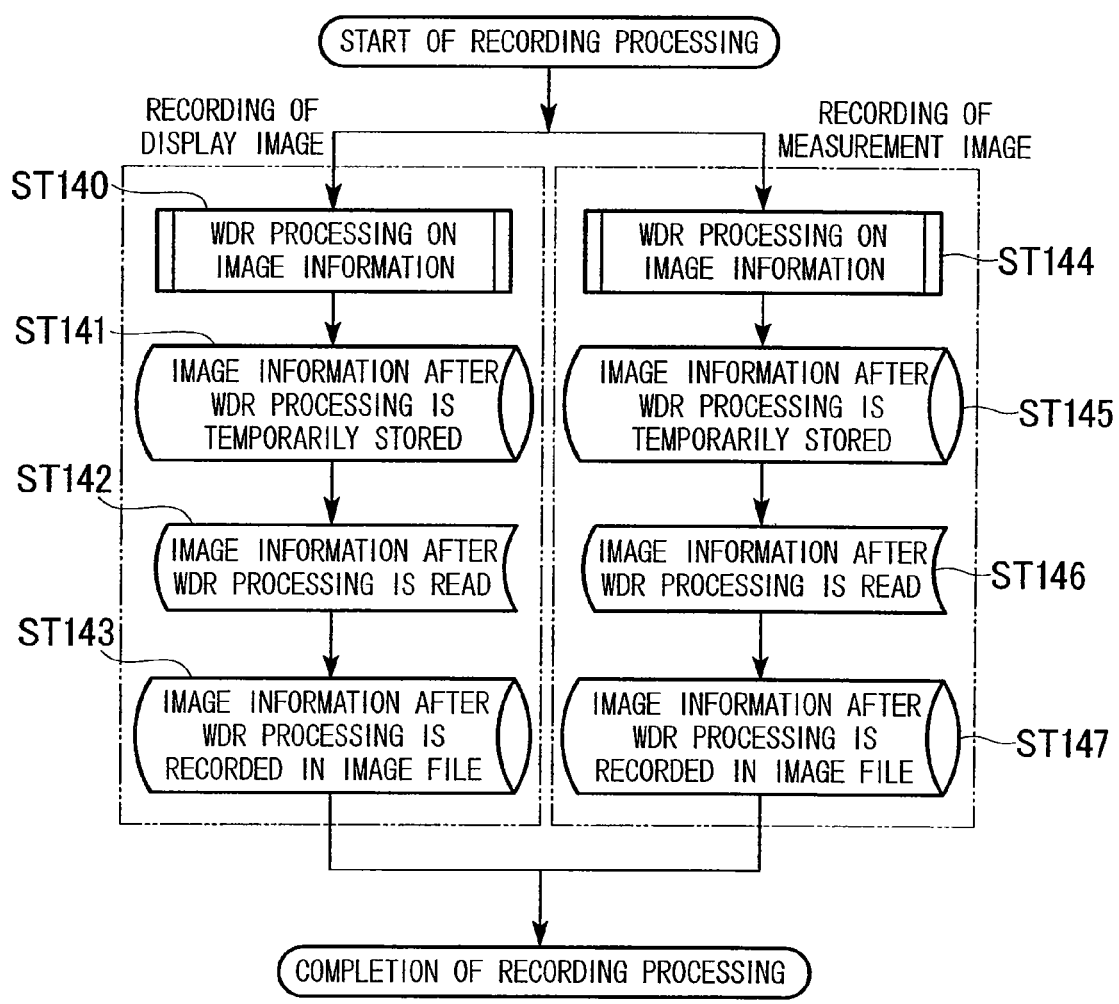
FIG. 11 is a flow chart illustrating an operation of recording processing of the image measuring apparatus according to an embodiment of the invention.
Figure 12:
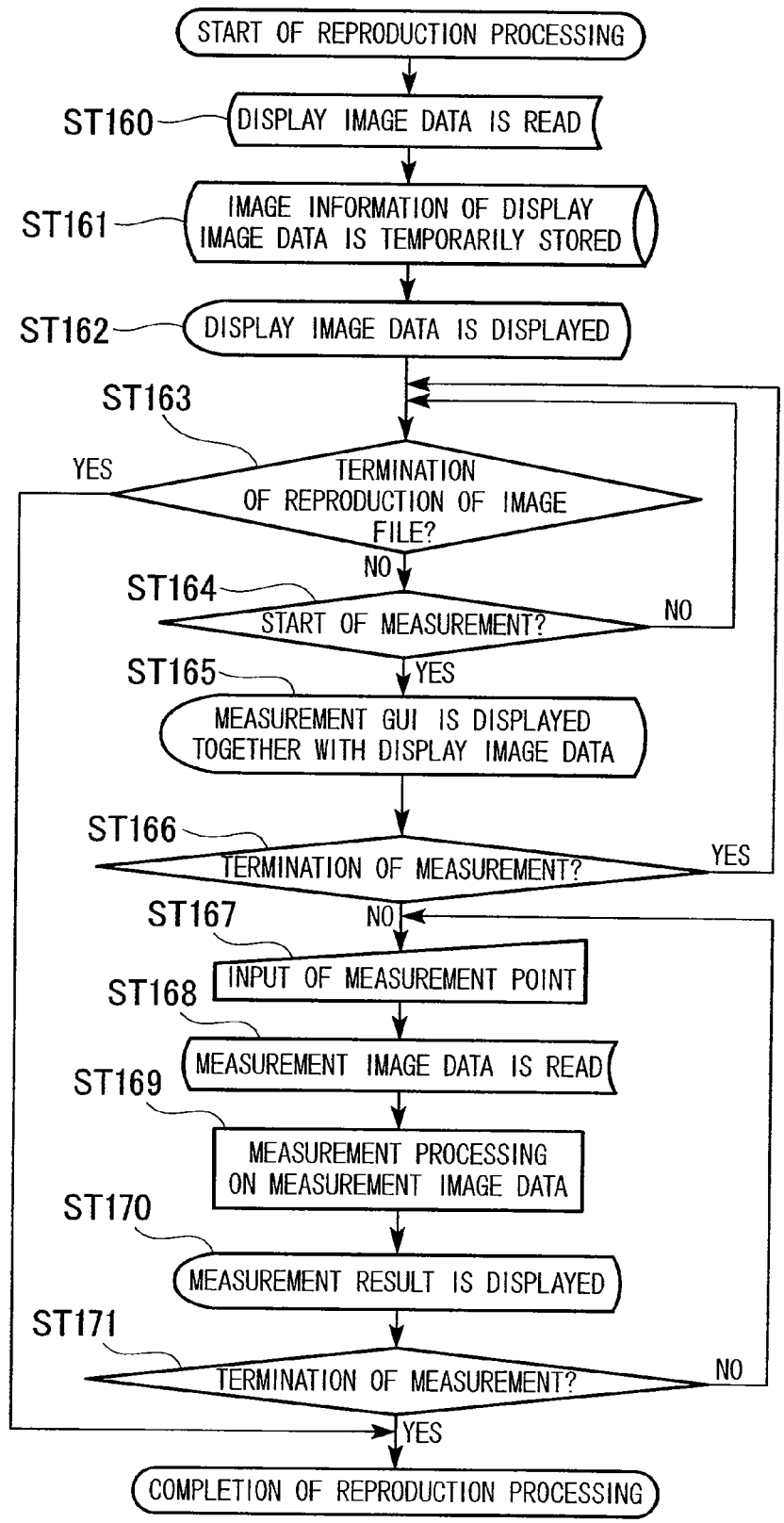
FIG. 12 is a flow chart illustrating an operation of reproduction processing of the image measuring apparatus according to an embodiment of the invention.

FIG. 7 is a flow chart illustrating an operation of the image measuring apparatus according to an embodiment of the invention. FIG. 8 is an explanatory view schematically illustrating an example of a display screen in an image display mode of the image measuring apparatus according to an embodiment of the invention. FIG. 9 is a flow chart illustrating an operation of measurement processing of the image measuring apparatus according to an embodiment of the invention. FIGS. 10A and 10B are explanatory views schematically illustrating examples of a display screen in a measurement mode of the image measuring apparatus according to an embodiment of the invention. FIGS. 11 and 12 are flow charts illustrating operations of recording processing and image file reproduction processing of the image measuring apparatus according to an embodiment of the invention, respectively.

The measuring endoscope apparatus 1 is configured such that an image display mode that allows an image acquired through the optical adapter 2 for stereo measurement to be displayed on the LCD monitor 6 when the power is ON, and various kinds of processing modes corresponding to operation input are executed when the operation input occurs from an input unit, such as the remote controller 5. Hereinafter, modes in which measurement processing, image information recording processing, and image file reproduction processing are performed will be described as examples of the various kinds of processing modes.

First, as shown in FIG. 7, image information corresponding to one frame is acquired from the image acquiring section 30 in step ST101. That is, the input image data 100 acquired from the image acquiring section 30 is transmitted to the preprocessing section 35 of the control unit 4, and the one-frame input image data 100a which has been properly subjected to preprocessing by means of the preprocessing section 35 is acquired as image information.

Next, in step ST102, image processing selected beforehand by the remote controller 5 or the like is selected and the selected image processing is set in the image processing section 34 in the processing selection section 40.

Then, in step ST103, the CPU 10 checks whether or not an operation input has been performed. If the operation input has been performed, processing corresponding to each operation input is executed. For example, in the case when an operation input for starting measurement is performed, the process proceeds to step ST106. In addition, if an operation input for recording image information in an image file to be described later is performed, the process proceeds to step ST107. In addition, if an operation input for reproducing an image recorded in the image file to be described later is performed, the process proceeds to step ST108.

On the other hand, in the case when the operation input is not performed, the process proceeds to step ST104.

In step ST104, current image processing set in the image processing section 34 is performed with respect to the one-frame input image data 100a, thereby generating the output image data 101A. In this case, if the processing (0) is set as the current image processing, image processing is cancelled without performing image processing, such as WDR processing.

Then, in step ST105, the output image data 10A generated in step ST104 is transmitted to the signal conversion section 38, and the display image data 101a in which other image data is properly combined is transmitted from the signal conversion section 38 to the display 33. Thus, the image information acquired in the image acquiring section 30 is displayed on the display 33.

Then, the process proceeds to step ST101 in which image information corresponding to following one frame is acquired, and then the procedures described above are repeated. As a result, when an operation input does not occur, an image display mode that allows an image corresponding to each frame, which has been subjected to the current image processing and is to be displayed on the display 33 in approximately real-time manner, is realized.

FIG. 8 is a view illustrating an example of a display screen in the image display mode.

As shown in FIG. 8, in the image display mode, a display screen 60 includes: a display region provided in the shape of an 'I' in upper, lower, and middle parts of a screen of the LCD monitor 6; and two approximately rectangular display regions excluding the I-shaped display region. Referring to FIG. 8, a parallax image 61L in the left approximately rectangular display region and a parallax image 61R in the right approximately rectangular display region are displayed in approximately real-time manner. The parallax images 61L and 61R are a pair of parallax images that are acquired at the same time through the object lenses 2B and 2A of the optical adapter 2 for stereo measurement, respectively.

In the example shown in FIG. 8, an object 62 having a three-dimensional shape, for example, a turbine blade train is displayed on the lower half of each of the approximately rectangular display regions.

In addition to those described above, image information, text information, and the like may be appropriately displayed together on the display screen 60. In the present embodiment, current date and time are displayed as date and time information 63 in the bottom region of the parallax image 61L in a real-time manner.

Next, a flow will be described in the case when the operation input has been performed in step ST103 of FIG. 7.

First, when an operation input that starts measurement is performed, that is, when the measurement start signal 103 is input from the measurement operation section 31, a flow of measurement processing, which is shown in steps ST110 to ST120 of FIG. 9, is executed as step ST106. However, processing in steps ST10 to ST112 is processing for generating the output image data 101A and processing in steps ST113 and ST114 is processing for generating the output image data 101B, and thus the processing in steps ST110 to ST112 and processing in steps ST113 and ST114 are executed simultaneously and in parallel through two system lines.

In step ST110, the current image processing set in the image processing section 34 is performed with respect to the one-frame input image data 100a to thereby generate the output image data 101A, in the same manner as step ST104 of FIG. 7.

Then, in step ST111, the output image data 101A is transmitted to the signal conversion section 38, is converted into the display image data 101a, and is then displayed as a still image on the display 33.

Then, in step ST112, the measurement GUI image 109 generated in the measurement section 43 is transmitted to the signal conversion section 38 and displayed on the display 33 together with the still image.

A display screen 60A at the start of measurement is shown in FIG. 10A.

In addition to the parallax images 61L and 61R and the date and time information 63 on the display screen 60, a cursor 68, an operation icon 65, a zoom window 66, measurement condition information 64, message information 67, and the like are displayed together on the display screen 60A so as to correspond to the measurement GUI image 109.

The cursor 68 serves to input a measurement point on the display screen 60A in response to an operation input from the measurement operation section 31, or serves to perform an operation, such as selection of an icon or menu.

The operation icon 65 includes a group of icons arranged in a middle display region of the display screen 60A. As an example, in the present embodiment, the operation icon 65 includes a measurement icon 65a for executing a measurement operation after inputting a measurement point with the cursor 68, a measuring mode switching icon 65b for setting types of measurement operations executed at the time of clicking the measurement icon 65a, for example, distance ('Distance'), angle, or the like, a clear icon 65c for clearing the display screen, a termination icon 65d for terminating measurement processing, and a modification icon 65e for modifying a measurement point.

The zoom window 66 serves to display an image around the cursor 68 in an enlarged manner.

The measurement condition information 64 indicates information on current measurement conditions. In the present embodiment, the measurement condition information 64 indicates, as an example, the type of the optical adapter 2 for stereo measurement that is being used.

The message information 67 indicates information on operation or measurement as various kinds of text information and numerical information. For example, an operation guide is displayed in FIG. 10A.

On the other hand, in step ST113, image processing selected on the basis of the measurement start signal 103 is performed on the input image data 100a by means of the image processing section 34, thereby generating the output image data 101B.

Then, in step ST114, a one-frame image based on the output image data 101B is temporarily stored in the image storage section 42.

As shown in FIG. 9, after steps ST112 and ST114 are completed, the process proceeds to step ST115.

In step ST115, it is checked whether or not an operator has performed an operation input for terminating the measurement through the measurement operation section 31.

If the operation input for terminating the measurement is performed, the measurement processing mode is ended to then proceed to step ST101 of FIG. 7. Thus, the mode shifts to an image display mode, such that an operation for acquiring image information corresponding to a next frame is performed.

If the operation input for terminating the measurement has not been performed, the process proceeds to step ST116.

In step ST116, a message that requests a measurement point to be input is displayed as the message information 67, such that a measurement point is input. The operator can input a measurement point by moving the cursor 68 to select the position on a screen by means of the measurement operation section 31 while observing the display screen 60A of the display 33. At this time, since an enlarged image around the cursor 68 is displayed on the zoom window 66, the detailed position of a measurement point can be selected on the zoom window 66 while checking the overall position on the parallax image 61L.

In this case, images based on the output image data 101A, for which image processing set beforehand by the image processing selection operation section 32 has been performed, are displayed on the display screen 60A as the parallax images 61L and 61R and the zoom window 66. Accordingly, it becomes easy to input a measurement point.

In addition, whenever a position is selected, coordinate information on the parallax image 61L is acquired. For example, as shown in FIG. 10B, images, such as X-shaped click display positions 69a and 69b, overlap the parallax image 61L and coordinate information of the click position of the cursor 68 is acquired. Here, the selection of a measurement point on the parallax image 61L, which serves as an image for measurement point input, is just an example. Alternatively, a measurement point may be selected on the parallax image 61R.

For example, in the case of distance measurement, processing in step ST116 is completed by specifying two positions as described above and then operating the measurement icon 65a, the flow proceeds to step ST117.

In step ST117, the measurement section 43 reads an image based on the output image data 101B, which is temporarily stored in step ST114, from the image storage section 42.

Then, in step ST118, the measurement section 43 sets the output image data 101B, which is read in step ST117, as image data to be measured and performs measurement processing corresponding to the measurement point input in step ST116 with respect to the image data. At this time, the output image data 101B has been subjected to image processing (also including the processing (0) in which the WDR processing is cancelled), which is selected corresponding to a desired measurement accuracy condition, by means of the processing selection section 40. Accordingly, it is possible to perform the measurement processing without causing the measurement accuracy to lower due to the image processing performed on the parallax images 61L and 61R displayed on the display 33.

Then, in step ST119, a result of the measurement processing performed in step ST118 is transmitted as the measurement result information 102 to the signal conversion section 38 and is displayed as measurement result information 70 as shown in FIG. 10B. For example, a measurement distance L is displayed like 'L=3.24 mm'.

Then, in step ST120, it is checked whether or not an operation for terminating the measurement has been performed like step ST115.

In the case when it is checked that the operation for terminating the measurement is not performed, the process proceeds to step ST116.

If it is checked that the operation for terminating the measurement has been performed, the measurement processing is terminated, the flow proceeds to step ST101 of FIG. 7.

Then, in step ST103 of FIG. 7, if an operation input for recording image information is performed, a flow of steps ST140 to ST143 shown in FIG. 11 is executed as step ST107.

In step ST140, the current image processing set in the image processing section 34 is performed with respect to the one-frame input image data 100a to thereby generate the output image data 101A, in the same manner as step ST104 of FIG. 7. Moreover, in one system line of the image processing section 34, image processing selected on the basis of the measurement start signal 103 is performed to generate the output image data 100B. Then, the image processing section 34 transmits the output image data 101A to the signal conversion section 38 so as to be displayed on the display 33 and also transmits the output image data 101A and 101B to the image storage section 42.

Then, in step ST141, the output image data 101A and 101B are temporarily stored as still images in the image storage section 42.

Then, in step ST142, the output image data 101A and 101B are read from the image storage section 42.

Then, in step ST143, the output image data 101A and 101B are recorded as an image file in the external storage medium 44, such as the PCMCIA memory card 18 or the compact flash (registered trademark) memory card 19, connected to the PC card I/F 13. In this case, the output image data 101A and 101B can be recorded in one image file so as to be distinguished from each other. Hereinafter, the output image data 101A on the image file is referred to as display image data 120A and the output image data 101B is referred to as measurement image data 120B. The measurement image data 120B is recorded in a region of an image file that is not usually displayed, for example, the Exif header.

Each image data recorded in the image file allows display on the display 33 and image measurement to be performed when image file reproduction processing to be mentioned later is executed.

Thus, the recording processing is completed, the flow proceeds to step ST101 of FIG. 7.

In addition, in the recording processing, the output image data 101A and 101B may not necessarily be generated simultaneously and in parallel, since it is sufficient that the output image data 101A and 101B are recorded in an image file in the proper order. For example, it may be possible to generate an output image data and then generate the other output image data.

Alternatively, it is possible to make a modification in which an output image data is first generated in step ST140 and then steps ST141 to ST143 are executed, then the process proceeds to step ST140 to generate the other output image data and then steps ST141 to ST143 are executed, and then recording processing is completed.

Then, in step ST103 of FIG. 7, if an operation input for reproducing an image recorded in an image file is performed, a flow of steps ST160 to ST171 shown in FIG. 12 is executed as step ST108.

In step ST160, a proper selection menu, such as an image file list, is displayed on the display screen 60 such that image data to be reproduced can be selected using the remote controller 5 or the like, and the selected image data is read as the display image data 120A into the image storage section 42. Here, the display image data 120A is the same as the output image data 101A at the time of recording.

Then, in step ST161, the display image data 120A is temporarily stored in the image storage section 42. Then, in step ST162, the display image data 120A is transmitted from the image storage section 42 to the signal conversion section 38 and is then displayed as the display image data 101a on the display 33.

Unlike the image display mode, the display screen is not displayed in a real-time manner. Except for a still image, the display screen is the same as the display screen 60 shown in FIG. 8. Here, the date and time information 63 may be appropriately modified, for example, by displaying the date and time at the time of recording or displaying proper text information for identifying an image file or an icon indicating an image reproduction mode on the display screen 60.

Then, in step ST163, it is checked whether or not an operation input for terminating reproduction of an image file has been performed through the measurement operation section 31.

If the operation input for terminating the reproduction of the image file has been performed, the reproduction processing is completed, the flow proceeds to step ST101 of FIG. 7.

Thus, for example, in the case when an operator desires to observe an image of an object recorded in the past on the display 33, the operator may perform an operation input for terminating reproduction of an image file after observing the image to then return to the image display mode.

In addition, if the operation input for terminating the reproduction of an image file is not performed, the process proceeds to step ST164.

In step ST164, it is checked whether or not the operator has performed an operation input for starting the measurement through the measurement operation section 31.

If the operation input for starting the measurement has been performed, the process proceeds to step ST165.

If the operation input for starting the measurement has not been performed, the process proceeds to step ST163.

Steps ST165 to ST171 are the flow of measurement processing for performing image measurement by setting the display image data 120A read from an image file as an image for measurement point input and reading the measurement image data 120B from the image file as image data to be measured. Hereinafter, measurement processing in steps ST165 to ST171 will be described focusing on differences from the measurement processing in steps ST112 to ST120 of FIG. 9.

In step ST165, the same processing as in step ST112 of FIG. 9 is performed, such that a display screen approximately equal to that in FIG. 10A is displayed on the display 33. However, in step ST165, the parallax images 61L and 61R corresponding to the display image data 120A displayed in step ST162 are displayed together with the measurement GUI image 109, and display of the date and time information 63, the measurement condition information 64, and the like may be properly modified.

Then, in step ST166, it is checked whether or not the operator has performed an operation input for terminating the measurement through the measurement operation section 31.

If the operation input for terminating the measurement has been performed, the measurement processing is terminated, the flow proceeds to step ST163.

If the operation input for terminating the measurement has not been performed, the process proceeds to step ST167.

Then, in steps ST167 to ST170, processing is performed for reading the output image data 101A as the display image data 120A and the output image data 101B as the measurement image data 120B in steps ST116 to ST119 of FIG. 9. In this case, an image corresponding to the measurement image data 120B is used as the parallax images 61L and 61R on the display screen 60 of FIGS. 10A and 10B. For example, the date and time information 63, the measurement condition information 64, and the like are appropriately modified.

By executing the processing in steps ST167 to ST170, various kinds of measurement processing can be performed using the measurement image data 120B, which is based on the output image data 101B at the time of recording, as image data to be measured.

Then, in step ST171, it is checked whether or not an operation for terminating the measurement has been performed like step ST114.

If it is checked that the operation for terminating the measurement is not performed, the process proceeds to step ST167.

If it is checked that the operation for terminating the measurement has been performed, the image file reproduction processing and measurement processing using an image reproduced from an image file are terminated, the flow proceeds to step ST101 of FIG. 7.

In the above description, the display image data 120A is read from the image file in step ST161 and the measurement image data 120B is read from the image file in step ST168. However, the display image data 120A and the measurement image data 120B may be read and temporarily stored in step ST161. In this case, a process of step ST168 may be omitted.

Thus, in the measuring endoscope apparatus 1 according to the present embodiment, an image recognizable easily can be displayed through the WDR processing at the time of input of a measurement point. As a result, a measurement point can be input with high precision. Furthermore, in the case when selected image processing does not satisfy a predetermined measurement accuracy condition, the image processing is automatically changed on the basis of information of the image processing selection table 41. As a result, image measurement can be performed with the measurement accuracy set beforehand.

Next, a first modified example of the present embodiment will be described.

In this modified example, an operator can select a measurement accuracy condition, which is set in advance before acquiring image data to be measured, after the initial setting. In addition, measurement accuracy condition information 108 (refer to a two-dot chain line in FIG. 3) as well as the measurement start signal 103 can be transmitted to a measurement image acquiring section 39 from the measurement operation section 31 in the embodiment. In addition, in the processing selection section 40 of the measurement image acquiring section 39, image processing that satisfies the measurement accuracy condition information 108 is selected referring to the image processing selection table 41 and the control signal 104 is transmitted.

The measurement accuracy condition information 108 may be input as a numeric value of the measurement accuracy using the remote controller 5 or may be selected from an operation menu displayed on the LCD monitor 6.

Further, measurement accuracy conditions set when initializing a measurement condition are used in the case when there is no input of the measurement accuracy condition information 108 or when a default value is designated on an operation menu. In the modified example, an operator can select a measurement accuracy condition before acquiring image data to be measured. Therefore, it is possible to easily change the measurement accuracy according to the requirements of measurement.

Next, a second modified example of the present embodiment will be described.

Figure 13:
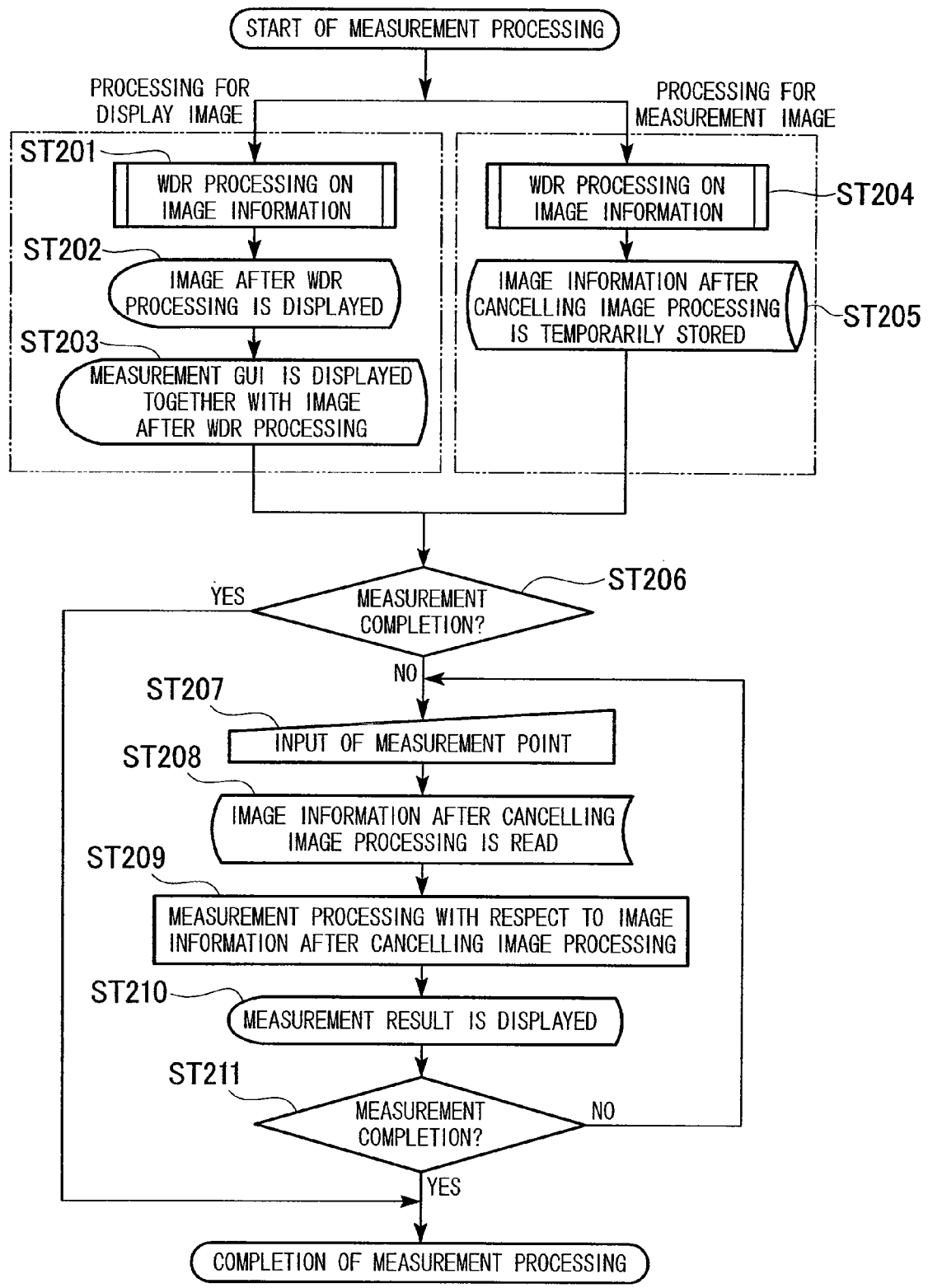
FIG. 13 is a flow chart illustrating measurement processing in an image measuring apparatus according to a second modified example of an embodiment of the invention.
Figure 14:
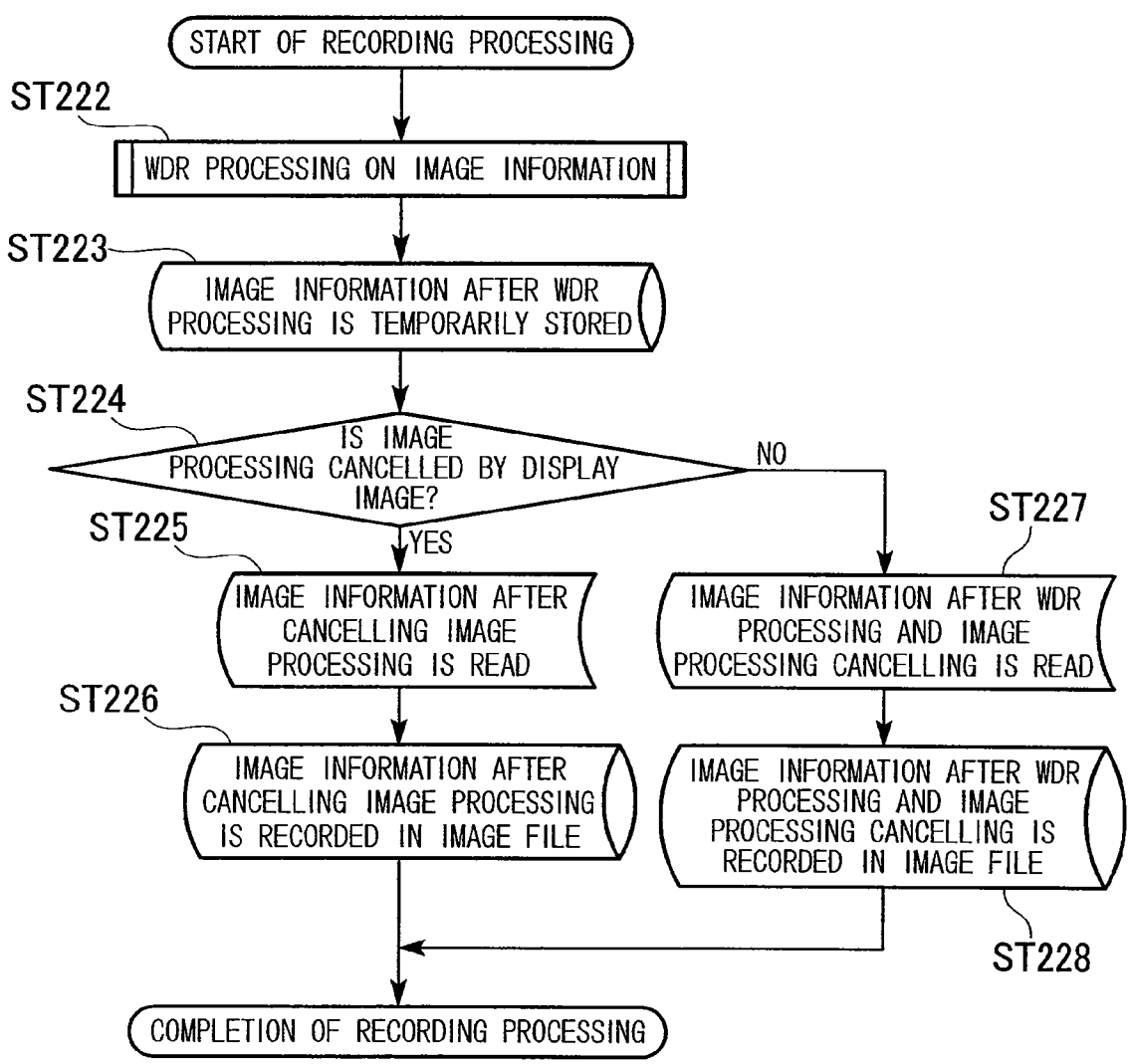
FIG. 14 is a flow chart illustrating recording processing in the image measuring apparatus according to the second modified example of an embodiment of the invention.
Figure 15:
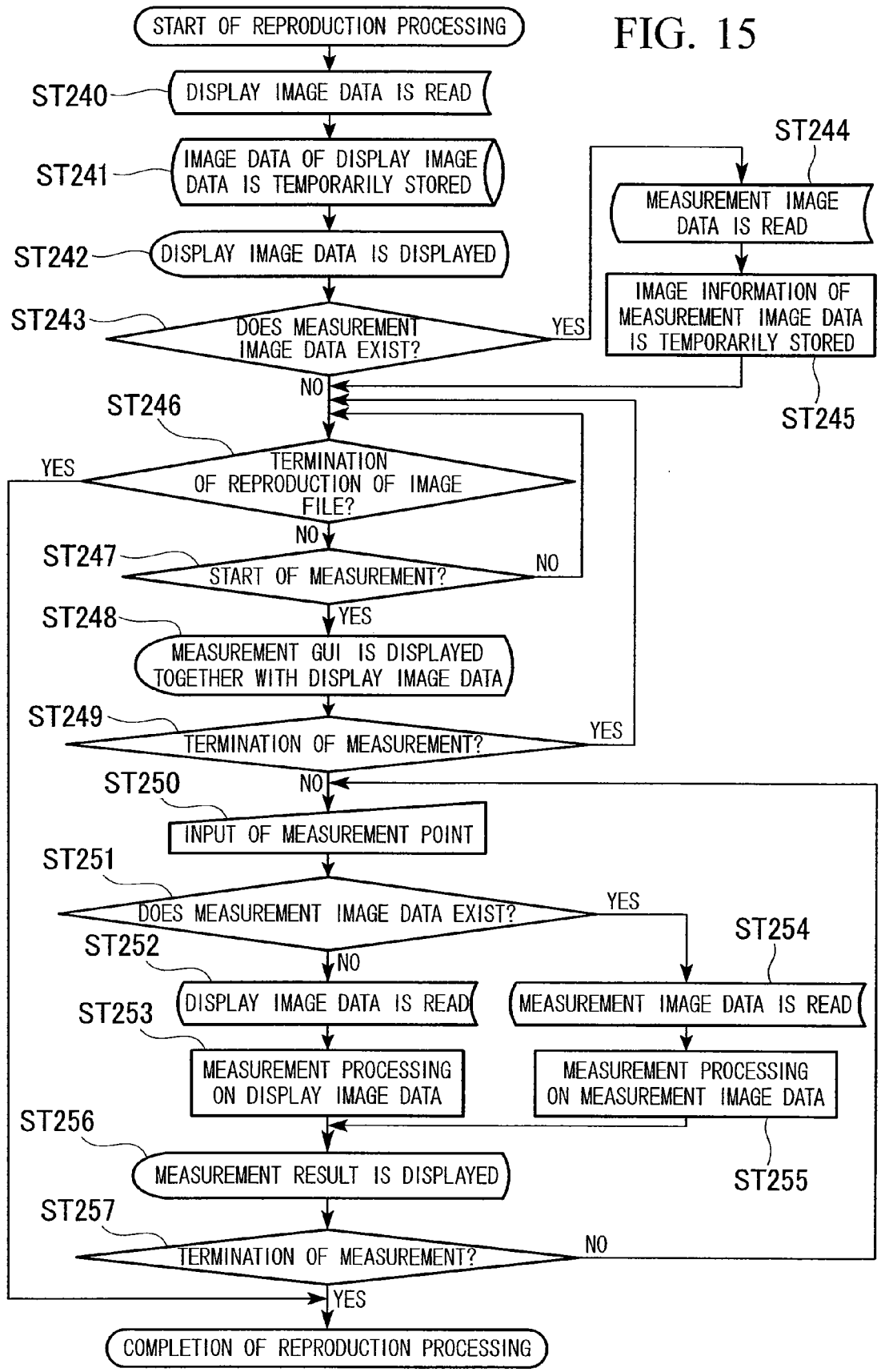
FIG. 15 is a flow chart illustrating image file reproduction processing in the image measuring apparatus according to the second modified example of an embodiment of the invention.

FIG. 13 is a flow chart illustrating measurement processing in an image measuring apparatus according to the second modified example of an embodiment of the invention. FIG. 14 is a flow chart illustrating recording processing in the image measuring apparatus according to the second modified example of an embodiment of the invention. FIG. 15 is a flow chart illustrating reproduction processing in the image measuring apparatus according to the second modified example of an embodiment of the invention.

In the above description of the embodiment, a case in which image processing is cancelled by selecting the processing (0) is included. However, in this modified example, efficient processing is realized in the case when cancelling of the image processing is selected, and only the flow of measurement processing, recording processing, and image file reproduction processing in the above embodiment is modified. Hereinafter, it will be described about an operation in only a case in which the processing (0) is executed as image processing that is executed in steps ST106 and ST13 of FIG. 9 in the above embodiment.

In the modified example, steps ST280, ST281, and ST282 are executed instead of the measurement processing (ST106 of FIG. 7), the recording processing (ST107 of FIG. 7), and the image file reproduction processing (ST108 of FIG. 7), respectively. Processing in steps ST280 and ST281 (refer to FIG. 7) is executed according to the flow shown in FIGS. 13 to 15, respectively. Hereinafter, it will be mainly described about a difference from the above description.

First, a flow of step ST280 that is measurement processing in this modified example will be described.

Step ST280 is executed as steps ST201 to ST211 shown in FIG. 13.

Processing in steps ST201 to ST203 is the same as the processing in steps ST110 to ST112 of FIG. 9, respectively.

Steps ST204 and ST205 are processing corresponding to steps ST113 and ST114 of FIG. 9, and the only difference is that the processing (0) which cancels image processing is executed on the input image data 100*a*.

For this reason, in step ST205, the input image data 100*a* as the output image data 101B is stored as still image data in the image storage section 42.

After steps ST203 and ST205 are completed, the process proceeds to ST206.

Processing in steps ST206 to ST211 is the same as the processing in steps ST114 to ST119 of FIG. 9, respectively. However, a difference is that still image data for which image processing is cancelled is read as the output image data 101B to perform the measurement processing in steps ST208 and ST209.

In the measurement processing in the modified example, an operator sets a measurement point while observing an image, which has been subjected to appropriate image processing, on the display 33, and accordingly, the measurement can be performed conveniently. On the other hand, since actual measurement processing is performed using the output image data 101B, which is the same as the input image data 100*a* which is not subjected to image processing that lowers the measurement accuracy, as image data to be measured, the measurement can be performed satisfactorily.

Next, a flow will be described with respect to step ST281 that is recording processing in the modified example.

Step ST281 is executed as steps ST222 to ST228 shown in FIG. 14.

Processing in steps ST222 and ST223 is the same as the processing in steps ST140 and ST141 of FIG. 11, respectively, and the only difference is that the processing (0) for cancelling image processing is executed on the input image data 100a so as to generate the output image data 101B in step ST222.

For this reason, in step ST223, the output image data 101A subjected to the current image processing is temporarily stored as still image data in the image storage section 42, and the input image data 100a as the output image data 101B is temporarily stored as still image data in the image storage section 42.

Then, in step ST224, it is checked whether or not the image processing is cancelled by the output image data 101A generated in step ST222.

In the case when the image processing is cancelled, the process proceeds to step ST225.

In the case when the image processing is not cancelled, the process proceeds to step ST227.

In step ST225, for example, only the output image data 101A is read because image information and the output image data 101A and 101B temporarily stored in the image storage section 42 are the same as the input image data 100a.

Then, in step ST226, the read output image data 101A is recorded as the display image data 120A in an image file of the external storage medium 44.

Then, after the recording processing is completed, the process proceeds to step ST100 of FIG. 7.

On the other hand, in step ST227, the output image data 101A, which has been subjected to image processing other than the processing (0), and the output image data 101B, for which image processing is cancelled by the processing (0), are read from the image storage section 42.

Then, in step ST228, the read output image data 101A and 101B are recorded in an image file of the external storage medium 44. In that case, the output image data 101A and the output image data 101B are recorded in one image file as the display image data 120A and the measurement image data 120B, respectively.

The measurement image data 120B is recorded in a region of the image file that is not usually displayed, for example, the Exif header.

Then, after the recording processing is completed, the process proceeds to step ST101 of FIG. 7.

In the recording processing in the modified example, in the case when image processing is cancelled and the display image data 120A may also be used as image data that can be measured, only the display image data 120A can be recorded. Accordingly, the capacity of an image file can be reduced.

Moreover, in the case of image data for which image processing is cancelled, the image measurement can be performed without lowering the measurement accuracy due to the image processing.

Next, it will be described about a flow of step ST282 that is image file reproduction processing in the modified example.

Step ST282 is executed as steps ST240 to ST257 shown in FIG. 15.

Processing in steps ST240 to ST242 is the same as the processing in steps ST160 to ST162 of FIG. 12, respectively.

In step ST243, it is checked whether or not the measurement image data 120B corresponding to the display image data 120A exists in an image file of the external storage medium 44.

In the case when the measurement image data 120B corresponding to the display image data 120A displayed on the display 33 exists, different kinds of image processing are performed for the display image data 120A and the measurement image data 120B, and accordingly, the process proceeds to step ST244.

In the case when the measurement image data 120B corresponding to the display image data 120A displayed on the display 33 does not exist, the display image data 120A can be used as image data to be measured, and accordingly, the process proceeds to step ST246.

In step ST244, the measurement image data 120B is read from the external storage medium 44.

Next, in step ST245, the read measurement image data 120B is temporarily stored in the image storage section 42.

Then, the process proceeds to step ST246.

In step ST246, it is checked whether or not an operation input for terminating reproduction of an image file has been performed through the measurement operation section 31.

If the operation input for terminating the reproduction of the image file has been performed, reproduction processing is terminated, the flow proceeds to step ST101 of FIG. 7.

In addition, if the operation input for terminating the reproduction of the image file is not performed, the process proceeds to step ST247.

In step ST247, it is checked whether or not an operator has performed an operation input for starting measurement through the measurement operation section 31.

If the operation input for starting the measurement has been performed, the process proceeds to step ST248.

If the operation input for starting the measurement is not performed, the process proceeds to step ST246.

Steps ST249 to ST257 are the flow of measurement processing using an image read from the image file.

Hereafter, an explanation will be made focusing on the difference from processes of the measurement processing in steps ST112 to ST120 of FIG. 9 and steps ST165 to ST171 of FIG. 12.

Processing in steps ST248 to ST250 is the same as the processing in steps ST165 to ST167 of FIG. 12, respectively.

In this modified example, step ST251 is executed subsequent to step ST250.

In step ST251, it is checked whether or not the measurement image data 120B corresponding to the display image data 120A exists in an image file of the external storage medium 44.

If the measurement image data 120B does not exist, the process proceeds to step ST252.

If the measurement image data 120B exists, the process proceeds to step ST254.

In steps ST252 and ST253, processing is performed for rereading the output image data 101B as the display image data 120A in steps ST117 and ST118 of FIG. 9. Then, the process proceeds to step ST256 after completion of step ST253.

Furthermore, in steps ST254 and ST255, processing is performed for reading the output image data 101B as the measurement image data 120B in steps ST117 and ST118 of FIG. 9. Then, the process proceeds to step ST256 after completion of step ST255.

In step ST256, a result of the measurement processing in step ST253 or ST255 is transmitted as the measurement result information 102 to the signal conversion section 38 so as to be displayed as the measurement result information 70 as shown in FIG. 10B. For example, the measurement distance L is displayed like 'L=3.24 mm'.

Then, in step ST257, it is checked whether or not an operation for terminating the measurement has been performed.

If it is checked that the operation for terminating the measurement is not performed, the process proceeds to step ST250.

On the other hand, if it is checked that the operation for terminating the measurement has been performed, the measurement processing is terminated, the flow proceeds to step ST101 of FIG. 7.

Next, a third modified example of the present embodiment will be described.

Figure 16:
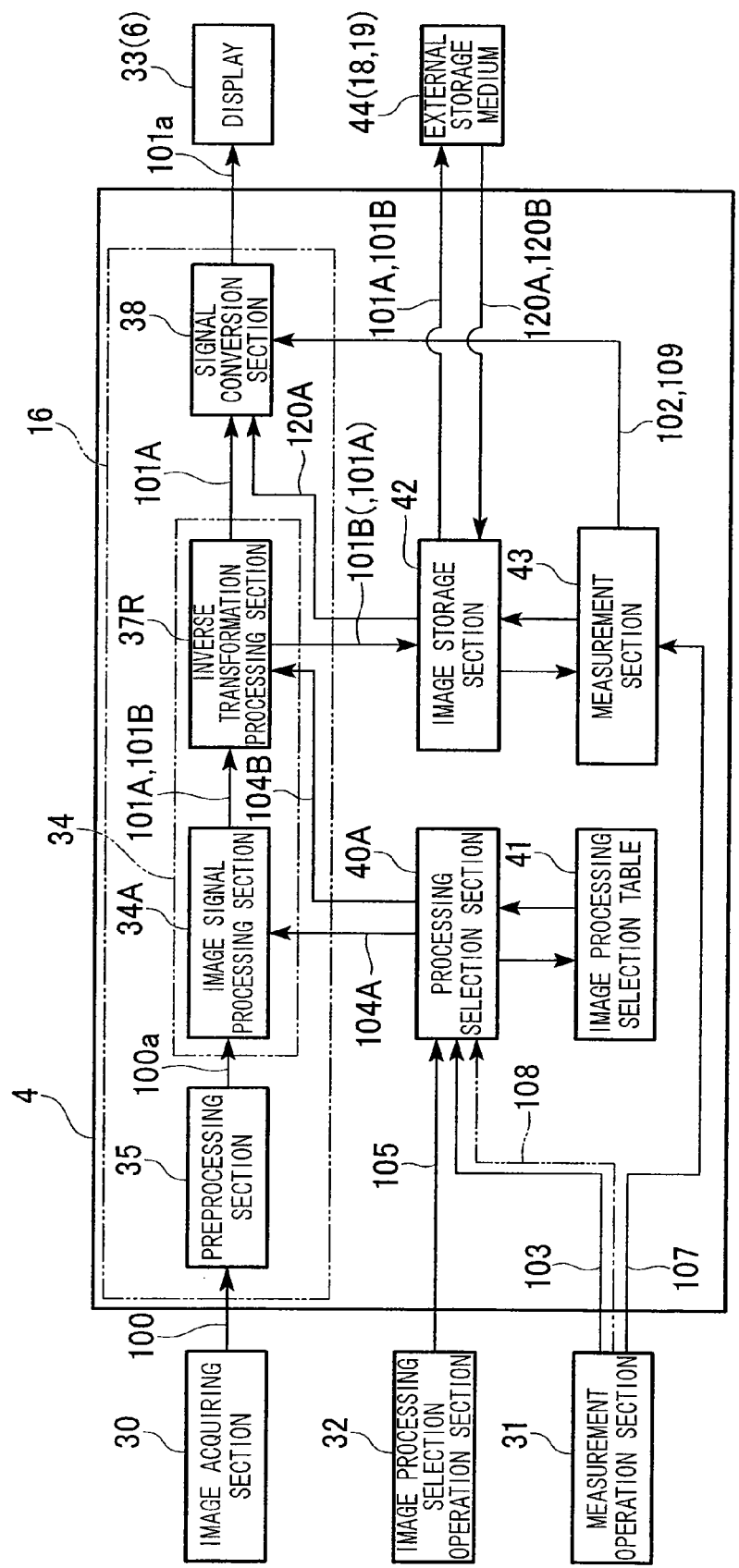
FIG. 16 is a functional block diagram illustrating the configuration of a functional block of a control unit of an image measuring apparatus according to a third modified example of an embodiment of the invention.

FIG. 16 is a functional block diagram illustrating the configuration of a functional block of a control unit of an image measuring apparatus according to a third modified example of an embodiment of the invention.

In this modified example, as shown in FIG. 16, the image processing section 34 in the above embodiment is configured to include an image processing section 34A and an inverse transformation processing section 37R, and accordingly, the processing selection section 40 is replaced with a processing selection section 40A. Hereafter, an explanation will be made focusing on the difference from the above embodiment.

Among the 'n' types of image processing of the image processing section 34, the image processing section 34A performs 'n−1' types of processing (1), . . . , processing (n−1) excluding the processing (0) that cancels image processing.

The processing selection section 40A transmits a control signal 104A, which selects the processing (1) to processing (n−1) according to setting of the control signal 105 and the measurement start signal 103, to the image processing section 34A and transmits a control signal 104B, which controls ON/OFF of the inverse transformation processing section 37R for each of the output image data 101A and 101B, to the inverse transformation processing section 37R.

When ON of the inverse transformation processing is designated for the output image data 101A (101B) by the control signal 104B, the inverse transformation processing section 37R performs inverse transformation processing for returning the output image data 101A (101B), which is generated by performing any of the image processing in the image processing section 34A, to the input image data 100a before processing. In addition, when OFF of the inverse transformation processing is designated for the output image data 101A (101B) by the control signal 104B, the inverse transformation processing section 37R performs processing for making the output image data 101A (101B) pass therethrough without inverse transformation.

The output image data 101A and 101B for which processing in the inverse transformation processing section 37R has been completed are transmitted to the signal conversion section 38 and the image storage section 42, respectively, in the same manner as that after the processing of the image processing section 34 in the above embodiment. In addition, in the case of image recording processing, the output image data 101A is transmitted even to the image storage section 42.

A case in which the inverse transformation processing is ON in the inverse transformation processing section 37R is the same as a case in which the image processing performed in the image processing section 34A is cancelled. Therefore, the inverse transformation processing section 37R in the modified example serves as an example of another implementation unit in the case of cancelling image processing using the image processing cancelling unit and has the same operation and effects as those in the above embodiment.

Next, a measuring operation of the modified example will be described.

Figure 17A:
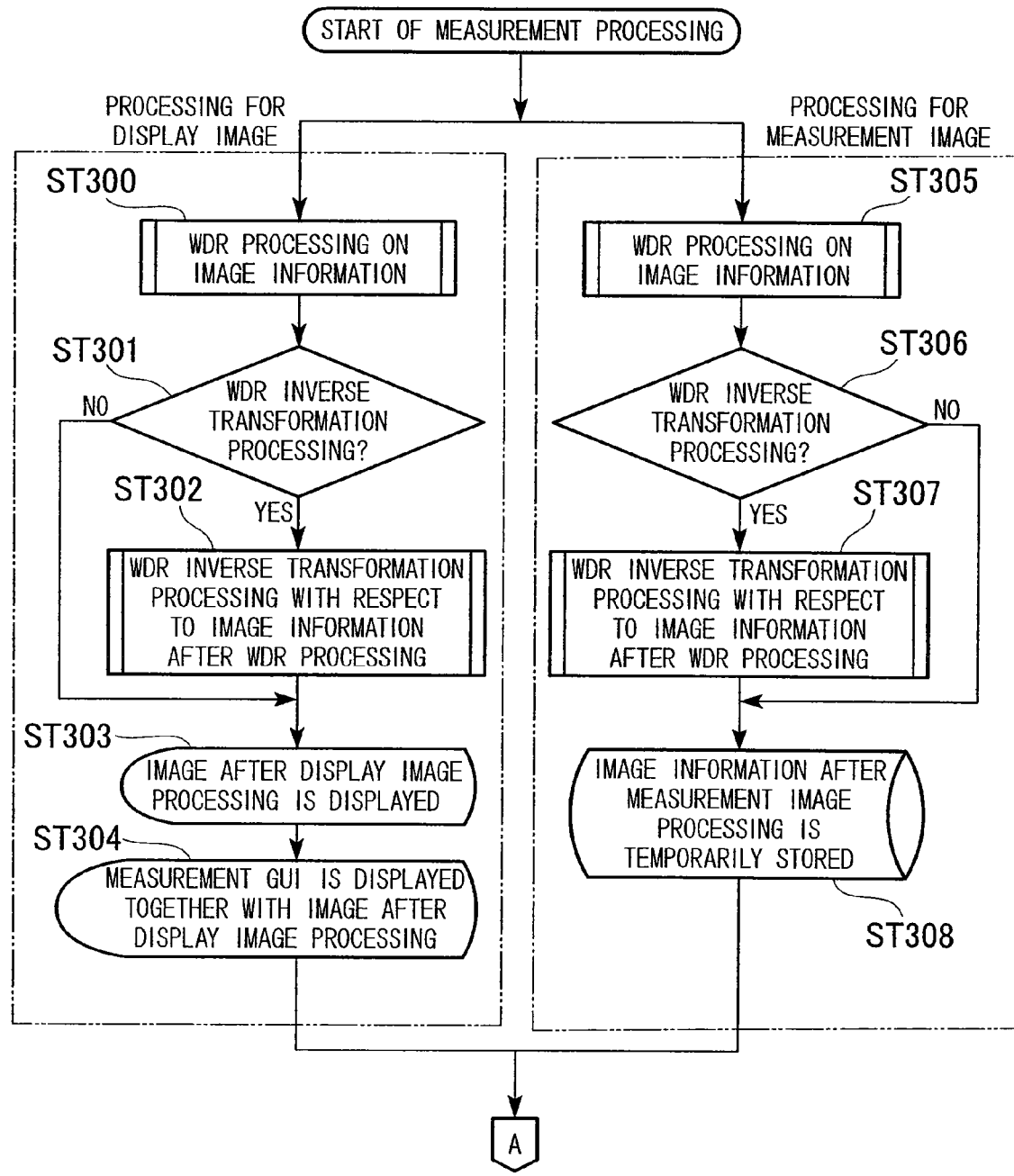
FIG. 17A is a flow chart illustrating an operation of measurement processing in the image measuring apparatus according to the third modified example of an embodiment of the invention.
Figure 17B:
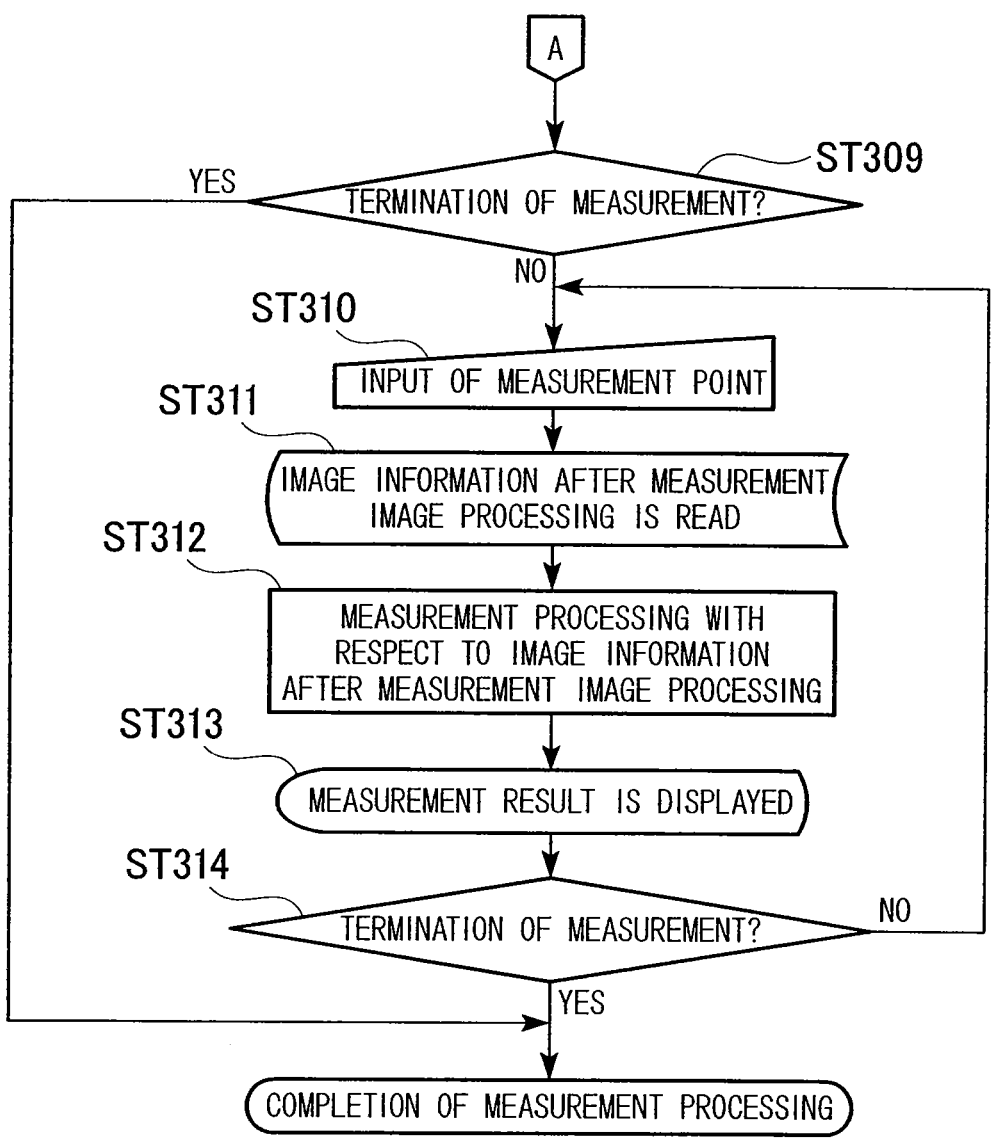
FIG. 17B is a flow chart illustrating an operation of the measurement processing in the image measuring apparatus according to the third modified example of an embodiment of the invention.
Figure 18:
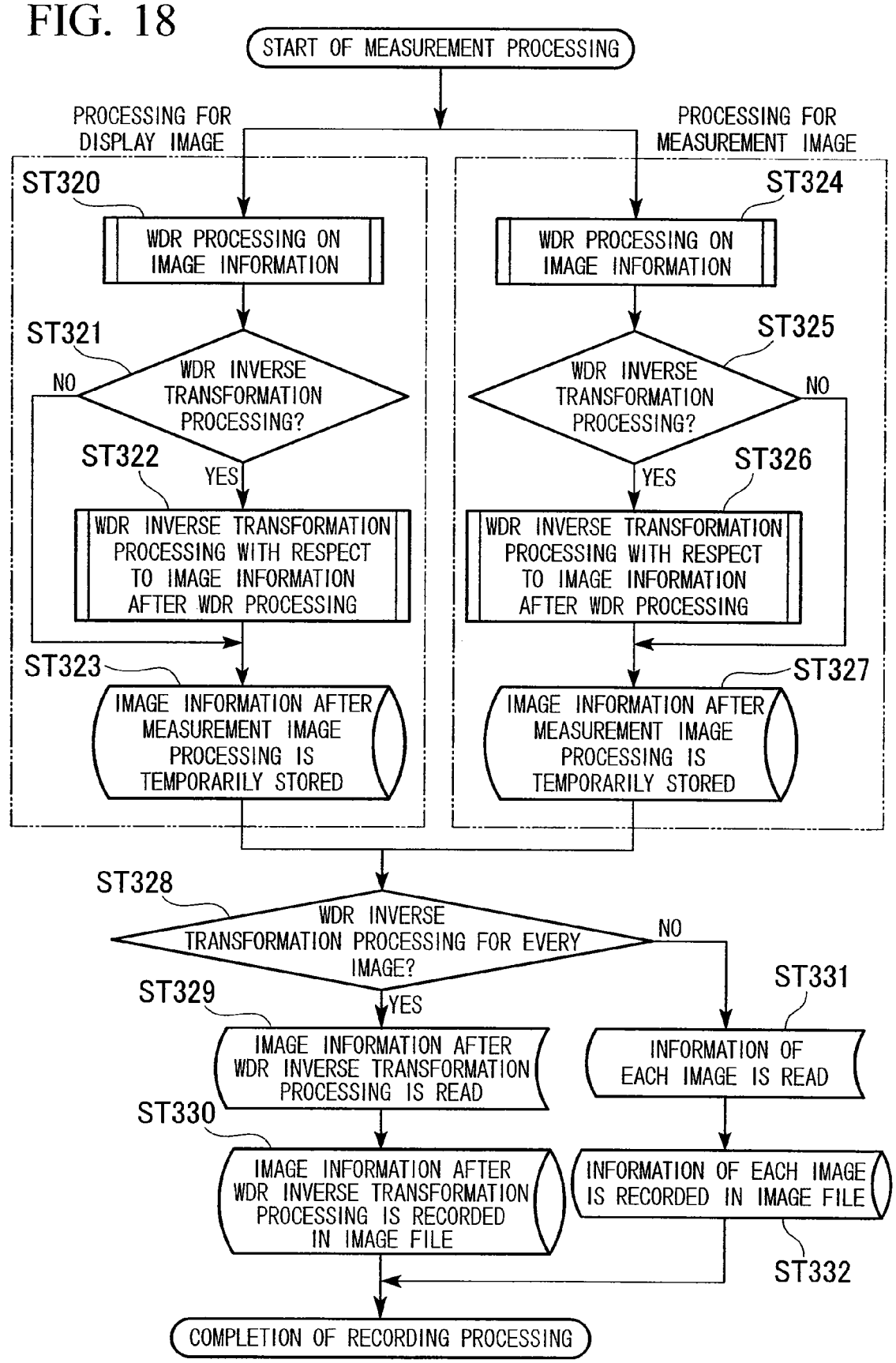
FIG. 18 is a flow chart illustrating an operation of recording processing in the image measuring apparatus according to the third modified example of an embodiment of the invention.

FIGS. 17A and 17B are flow charts illustrating an operation of measurement processing in the image measuring apparatus according to the third modified example of an embodiment of the invention. FIG. 18 is a flow chart illustrating an operation of recording processing in the image measuring apparatus according to the third modified example of an embodiment of the invention.

This modified example is the same as the above embodiment except that inverse transformation processing is ON in an image display mode in order to cancel image processing and is based on an operation according to the flow of FIG. 7. Hereinafter, the flow of steps ST290 and ST291 corresponding to ST106 and ST107 in the above embodiment will be described focusing on a difference from the above embodiment.

First, in the case when an operation input for starting measurement is performed, that is, when the measurement start signal 103 is input from the measurement operation section 31, the flow of steps ST300 to ST314 shown in FIGS. 17A and 17B is executed as ST290. In this case, processing in steps ST300 to ST304 is processing for generating the output image data 101A and processing in steps ST305 to ST308 is processing for generating the output image data 101B, and thus the processing in steps ST300 to ST304 and processing in steps ST305 to ST308 are executed simultaneously and in parallel through two system lines.

In step ST300, current image processing set in the image processing section 34A is performed on the input image data 100a corresponding to one frame and then the one-frame input image data 100a is transmitted as the output image data 101A to the inverse transformation processing section 37R.

Then, in step ST301, a determination on ON/OFF of the inverse transformation processing set by the control signal 104B in the inverse transformation processing section 37R is made.

In the case when the inverse transformation processing is ON, the process proceeds to step ST302.

In step ST302, inverse transformation of the image processing performed in step ST300 is performed with respect to the output image data 101A, the flow proceeds to step ST303.

In the case when the inverse transformation processing is OFF, the inverse transformation is not performed with respect to the output image data 101A that has been subjected to the image processing in step ST300, the flow proceeds to step ST303.

In step ST303, the output image data 101A which has been subjected to the inverse transformation processing or the output image data 101A which is not subjected to the inverse transformation processing is transmitted to the signal conversion section 38 and is then converts into the display image data 101a to be displayed on the display 33.

Then, in step ST304, the measurement GUI image 109 generated in the measurement section 43 is transmitted to the signal conversion section 38 so as to be also displayed on the display 33.

On the other hand, in step ST305, in the case when image processing selected on the basis of the measurement start signal 103 is designated for the input image data 100a or the measurement start signal 103 designates measurement processing based on the display image data 101a for the input image data 100a, the current image processing is performed to generate the output image data 101B.

Then, in step ST306, a determination on ON/OFF of the inverse transformation processing set by the control signal 104B in the inverse transformation processing section 37R is made.

In the case when the inverse transformation processing is ON, the process proceeds to step ST307. In step ST307, inverse transformation of the image processing performed in step ST305 is performed with respect to the output image data 101B, the flow proceeds to step ST308.

In the case when the inverse transformation processing is OFF, the inverse transformation is not performed with respect to the output image data 101A that has been subjected to the image processing in step ST307, the flow proceeds to step ST308.

In step ST308, a one-frame image based on the output image data 101B is temporarily stored in the image storage section 42.

After steps ST304 and ST308 are completed, the process proceeds to ST309, as shown in FIG. 17B.

Processing in steps ST309 to ST314 is the same as the processing in steps ST114 to ST119 of FIG. 9. However, in steps ST311 and 313, the image processing performed in step ST305 is inversely transformed as the output image data 101B according to the control signal 104B, and thus still image data for which image processing is cancelled is read and measurement processing is performed using the still image data as image data to be measured.

As described above, in the modified example, the measurement processing can be performed in the same manner as that in the above embodiment, since the inverse transformation processing section 37R is provided as an image processing cancelling unit.

Next, a flow will be described with respect to step ST291 which is recording processing in the modified example.

Step ST291 is executed as steps ST320 to ST332 shown in FIG. 18.

Processing in steps ST320 to ST322 is the same as the processing in steps ST300 to ST302 of FIG. 17, respectively.

In step ST323, the output image data 101A which has been subjected to the inverse transformation processing in step ST322 or the output image data 101A which is generated in step ST320 and is not subjected to the inverse transformation processing is temporarily stored in the image storage section 42.

On the other hand, processing in steps ST324 to ST327 is the same as the processing in steps ST305 to ST308 of FIG. 17, respectively.

After steps ST323 and ST327 are completed, the process proceeds to ST328.

In step ST328, it is checked whether or not both the output image data 101A and 101B stored in the image storage section 42 are subjected to inverse transformation processing.

In the case when the inverse transformation processing is performed, the process proceeds to step ST329.

In the case when the inverse transformation processing is not performed, the process proceeds to step ST331.

In step ST329, image processing for the output image data 101A and 101B and image information temporarily stored in the image storage section 42 are all cancelled, and accordingly, for example, only the output image data 101A is read because the output image data 101A and 101B and the image information are the same as the input image data 100a.

Then, in step ST330, the read output image data 101A is recorded as the display image data 120A in an image file of the external storage medium 44.

Then, after the recording processing is completed, the process proceeds to step ST101 of FIG. 7.

On the other hand, in step ST331, the output image data 101A and 101B are read from the image storage section 42.

Then, in step ST332, the read output image data 101A and 101B are recorded in an image file of the external storage medium 44. In this case, the output image data 101A and the output image data 101B are recorded in one image file as the display image data 120A and the measurement image data 120B, respectively.

The measurement image data 120B is recorded in a region of the image file that is not usually displayed, for example, the Exif header.

Then, after the recording processing is completed, the process proceeds to step ST101 of FIG. 7.

According to the recording processing in the modified example, the image processing is cancelled because the inverse transformation processing section 37R is used, in the same manner as the recording processing in the second modified example. Therefore, the recording processing in the third modified example has the same operation and effects as in the second modified example.

In addition, even in the third modified example, image file reproduction processing may be performed in the same manner as in the second modified example. Since the image file reproduction processing in the third modified example can be easily understood by applying the configuration of an image file and the measurement processing, which have been described in the image file reproduction processing in the second modified example, to the configuration of an image file and measurement processing in the recording processing in the third modified example, an explanation will be omitted.

Next, a fourth modified example of the present embodiment will be described.

In this modified example, a calibration setting unit is provided that performs calibration processing that allows the control unit 4 in the above embodiment to acquire the mask shape of the optical system of the optical adapter 2 for stereo measurement.

The same processing as that described in the embodiment can be applied as the calibration processing. The calibration setting unit is realized by causing the CPU 10 to execute a calibration processing program when a calibration mode is selected.

In the modified example, when a calibration mode is selected using the remote controller 5, for example, an object for calibration is imaged in the same manner as the case of image measurement in the above embodiment, image data that is a white image having the mask shape of the optical adapter 2 for stereo measurement is acquired as the output image data 101B, and operation processing on the acquired image data is performed by the calibration setting unit, such that calibration processing can be performed.

Thus, the calibration processing can be performed in a measurement accuracy condition set in advance without depending on image processing of an image displayed on the LCD monitor 6.

Further, even though the case in which the measurement image acquiring section includes the image processing selection table has been described as an example, other units may be used as long as the measurement accuracy corresponding to executable image processing can be obtained. For example, under the configuration in which an evaluation formula for calculating the corresponding measurement accuracy is obtained from data that specifies executable image processing and operation processing corresponding to the evaluation formula is performed, it is possible to adopt a unit that allows image processing to be selected by calculating the measurement accuracy from an operation result of the evaluation formula and then comparing the result.

Furthermore, even though the stereo measurement has been described as an example of image measurement, the optical adapter 2 for stereo measurement may be modified for other optical adapters in order to perform other image measurements. For example, it may be possible to select measurement points on the basis of brightness information of an image to be measured and to perform two-dimensional distance measurement between the measurement points. In this case, the position coordinates of the measurement points are acquired in a predetermined measurement accuracy condition by image processing. Accordingly, even if image processing for display that can be easily recognized is performed, it is possible to perform image measurement without being influenced by measurement error due to the image processing.

Furthermore, even though the case of using an endoscope as the image acquiring section has been described as an example, the image acquiring section is not limited to the endoscope. For example, other image acquiring sections, such as a microscope, may be used.

In addition, a case in which left and right parallax images are displayed at the same time when displaying an image on a display has been described as an example. However, as long as at least one of parallax images are displayed as an image for measurement point input, the image measurement can be performed. Accordingly, on a display screen at the time of image measurement, an image different from the image for measurement point input may be displayed on a screen corresponding to one of the parallax images 61L and 61R. For example, an image of image data to be measured, an image for which image processing is cancelled, or the like may be displayed.

In addition, only an image for measurement point input may be displayed on the entire display.

Moreover, even though the case in which display image data and measurement image data are recorded in one image file in the recording processing has been described as an example, the display image data and the measurement image data may be divided from each other to be stored in a plurality of image files as long as it is possible to recognize the correspondence of the display image data and the measurement image data.

Having described the preferred embodiments of the invention, the invention is not limited to the embodiments.

That is, addition, omission, and replacement of the configuration and other modifications could be made without departing from the spirit and scope of the invention. The invention is not limited by the above description but is defined by only the appended claims.

What is claimed is:

1. An image measuring apparatus comprising:
    an image acquiring section which includes an optical system for stereo measurement having two object lenses that are disposed so as to be spaced apart from each other, images an object, and generates input image data for one-frame including a pair of parallax images acquired by the two object lenses;
    a processing selection section that automatically selects a brightness gradation converting processing which satisfies a predetermined measurement accuracy condition among a plurality of the brightness gradation converting processing and sets the selected brightness gradation processing to a first brightness gradation converting processing;
    an image processing section which performs the first brightness gradation converting processing selected by the processing selection section to the input image data and generates output image data including the pair of the parallax images for a measurement operation and which performs a second brightness gradation converting processing that is different from the first brightness gradation converting processing to the input image data and generates output image data including the pair of the parallax images for a display;
    an input unit which performs an operation input to measure the object to be imaged for a measurement operation displayed on the display; and
    a measurement section which performs measurement of the object based on the operation input of the input unit to the output image data for a measurement operation generated by the image processing section;
    another of the first and second output image data for which image processing by the image processing section is different from that for the display image data based on the measurement operation on the input unit; and
    wherein
    the image measuring apparatus is configured such that the image processing operation does not change a parallax of the first output image data and of the second output image data.

2. The image measuring apparatus according to claim 1, wherein the image processing section includes an image processing cancelling unit that cancels an execution of the brightness gradation converting processing on the input image data.

3. The image measuring apparatus according to claim 1, further comprising:
    an image processing selection operation section that a user is capable of operating, that changes a direction in which an image for a measurement operation, displayed on the display, is viewed, and that outputs a control signal according to an operation of the user,
    wherein the processing selection section selects the second brightness gradation converting processing among the plurality of the brightness gradation converting processing based on the control signal output from the image processing selection operation section.

4. The image measuring apparatus according to claim 1, wherein the processing selection section contains an image processing selection table that stores measurement accuracy of image processing selectable in the image processing section.

5. The image measuring apparatus according to claim 1,
    wherein the image acquiring section is an endoscope containing at least an optical adaptor for stereo measurement, and
    the measurement section includes a calibration setting unit that performs calibration processing for acquiring the mask shape of an optical system of the endoscope.

6. The image measuring apparatus according to claim 1,
    wherein the brightness gradation converting processing performed by the image processing section is wide dynamic range processing.

7. An image measuring method comprising:
    an image acquiring step of imaging an object generating input image data for one-frame including a pair of parallax images acquired by two object lenses via an image acquiring section which includes an optical system for stereo measurement having the two object lenses which are disposed so as to be spaced apart from each other of an image measuring apparatus;
    a processing selection step of automatically selecting a brightness gradation converting processing satisfying a predetermined measurement accuracy condition among a plurality of the brightness gradation converting processing and sets the selected brightness gradation converting processing to a first brightness gradation converting processing by a processing selection section of the image measuring apparatus;

an image processing step of performing the first brightness gradation converting processing selected by the processing selection step to the input image data and generating output image data including the pair of the parallax images for a measurement operation and performing a second brightness gradation converting processing that is different from the first brightness gradation converting processing to the input image data and generating output image data including the pair of the parallax images for a display by an image processing section of the image measuring apparatus;

a display step of displaying image data for the measurement operation based on the output image data generated in the image processing step on a display of the image measuring apparatus;

an input step of performing an operation input to measure the object to be imaged for a measurement operation displayed on the display using an input unit of the image measuring apparatus; and a measurement step of performing measurement of the object based on the operation input of the input unit to the output image data for a measurement operation generated by the image processing step via a measurement section of the image measuring device apparatus.

8. The image measuring method according to claim 7, wherein the image processing step includes an image processing cancelling step of cancelling an execution of the brightness gradation converting processing on the input image data.

* * * * *